United States Patent
Levy et al.

(10) Patent No.: US 11,712,372 B2
(45) Date of Patent: Aug. 1, 2023

(54) WOUND COVERING APPARATUS

(71) Applicants: Avery Levy, Longboat Key, FL (US); Joan Esther Levy, Longboat Key, FL (US)

(72) Inventors: Avery Levy, Longboat Key, FL (US); Joan Esther Levy, Longboat Key, FL (US)

(*) Notice: Subject to any disclaimer, the term of this patent is extended or adjusted under 35 U.S.C. 154(b) by 0 days.

(21) Appl. No.: 17/713,886

(22) Filed: Apr. 5, 2022

(65) Prior Publication Data

US 2022/0241114 A1 Aug. 4, 2022

Related U.S. Application Data

(63) Continuation of application No. 17/022,623, filed on Sep. 16, 2020, now Pat. No. 11,291,589, which is a
(Continued)

(51) Int. Cl.
*A61F 13/02* (2006.01)
*A61F 13/00* (2006.01)
*A61F 15/00* (2006.01)

(52) U.S. Cl.
CPC .. *A61F 13/00072* (2013.01); *A61F 13/00063* (2013.01); *A61F 13/02* (2013.01);
(Continued)

(58) Field of Classification Search
CPC .. A61F 2013/00157; A61F 2013/00165; A61F 2013/00246; A61F 2013/00251;
(Continued)

(56) References Cited

U.S. PATENT DOCUMENTS 697,637 A * 4/1902 Lee .................... A61F 15/008
128/888
2,367,690 A 1/1945 Purdy
(Continued)

FOREIGN PATENT DOCUMENTS

| WO | WO 2000/043046 | 7/2000 |
| WO | WO 2017/041384 | 3/2017 |
| WO | WO 2018/191305 | 10/2018 |

OTHER PUBLICATIONS

PCT Application No. PCT/US2018/026964 International Preliminary Report on Patentability dated Oct. 15, 2019.
(Continued)

*Primary Examiner* — Camtu T Nguyen
(74) *Attorney, Agent, or Firm* — Polsinelli LLP

(57) ABSTRACT

The present disclosure relates to apparatus for covering a burn or other wound in ways that prevent or limit touching the wound. The present disclosure describes Burn Bandages that may include domes or structures that bridge over a wide range of a burn or wound size. In certain instances these structures may expand in one or more directions as they are adjusted to fit to a particular burn or wound size. Such bridging structures may include airways, openings, or voids that promote air/oxygen flow to the wound as the Burn Bandage sits upon surfaces or pads that contact healthy surrounding tissue while they cover a wound site. The apparatus may be any shape including, yet not limited to, a circle, a rectangle, a square, a hexagon, an octagon, an oval, a cone, a cylinder, have a semi-cylindrical shape, or that have any another geometric shape.

27 Claims, 19 Drawing Sheets

Side View 1310

Top View 1320

Related U.S. Application Data continuation of application No. 15/484,867, filed on Apr. 11, 2017, now abandoned.

(52) U.S. Cl.
CPC ........ *A61F 13/0233* (2013.01); *A61F 15/004* (2013.01); *A61F 2013/00157* (2013.01); *A61F 2013/00165* (2013.01); *A61F 2013/00182* (2013.01); *A61F 2013/00246* (2013.01); *A61F 2013/00251* (2013.01); *A61F 2013/00391* (2013.01); *A61F 2013/00578* (2013.01); *A61F 2013/00829* (2013.01)

(58) Field of Classification Search
CPC .. A61F 2013/00217; A61F 2013/00182; A61F 13/00063; A61F 13/00059
See application file for complete search history.

(56) References Cited

U.S. PATENT DOCUMENTS

| | | | |
|---|---|---|---|
| 2,443,140 A | 6/1948 | Larsen | |
| 2,579,403 A | 12/1951 | Slomowitz et al. | |
| 2,595,606 A | 5/1952 | Pohjola | |
| 2,785,677 A | 3/1957 | Stumpf | |
| 3,234,941 A | 2/1966 | Tucker | |
| 4,139,004 A | 2/1979 | Gonzalez | |
| 4,667,666 A | 5/1987 | Fryslie | |
| 4,745,946 A | 5/1988 | Seber | |
| 4,870,977 A * | 10/1989 | Imonti | A61F 15/008 623/7 |
| 5,144,958 A | 9/1992 | Krueger et al. | |
| 5,263,476 A | 11/1993 | Henson | |
| 5,961,480 A | 10/1999 | Augustine | |
| 6,051,249 A | 4/2000 | Samuelsen | |
| 6,107,536 A * | 8/2000 | Dadinis | A61F 15/008 602/44 |
| 6,274,787 B1 | 8/2001 | Downing | |
| 7,976,867 B2 | 7/2011 | Lundy et al. | |
| 8,784,392 B2 | 7/2014 | Vess et al. | |
| 11,291,589 B2 | 4/2022 | Levy | |
| 2003/0180341 A1 | 9/2003 | Gooch | |
| 2004/0143202 A1 | 7/2004 | Artenstein | |
| 2007/0161937 A1 | 7/2007 | Aali | |
| 2008/0045874 A1 | 2/2008 | An | |
| 2010/0081983 A1 * | 4/2010 | Zocher | A61F 15/008 602/54 |
| 2010/0198128 A1 | 8/2010 | Turnlund et al. | |
| 2013/0030341 A1 | 1/2013 | Freer | |
| 2014/0046263 A1 | 2/2014 | Salazar | |
| 2015/0005678 A1 | 1/2015 | Wall | |
| 2016/0030247 A1 | 2/2016 | Salvino | |
| 2018/0289556 A1 | 10/2018 | Levy | |
| 2018/0296405 A1 | 10/2018 | Raymond-Coblantz | |

OTHER PUBLICATIONS

PCT Application No. PCT/US2018/026964 International Search Report and Written Opinion dated Jun. 28, 2018.
U.S. Appl. No. 15/484,867 Final Office Action dated May 27, 2020.
U.S. Appl. No. 15/484,867 Office Action dated Dec. 31, 2019.
U.S. Appl. No. 15/484,867 Final Office Action dated Jan. 2, 2019.
U.S. Appl. No. 15/484,867 Office Action dated Feb. 28, 2018.

* cited by examiner

Leg Example 310

Arm Example 320

Side View 1310

Top View 1320

Leg Example 1410

Leg Example 1420

Side View 1510

Top View 1520

WOUND COVERING APPARATUS

CROSS-REFERENCE TO RELATED APPLICATIONS

The present application is a continuation and claims the priority benefit of U.S. patent application Ser. No. 17/022,623 filed Sep. 16, 2020, now U.S. Pat. No. 11,291,589, which is a continuation and claims the priority benefit of U.S. patent application Ser. No. 15/484,867 filed Apr. 11, 2017, the disclosures of which are incorporated herein by reference.

BACKGROUND OF THE INVENTION

Field of the Invention

The present invention is generally directed to bandages. More specifically, the present invention relates to bandages that protect a wound by minimizing physical contact of the wound.

Description of the Related Art

Bandages available for purchase today come in a few basic configurations that have been available for years. One of these basic configurations include bandages that are predominantly flat that include a portion of gauze and one or more adhesive portions. For example, the original Band-Aid™ brand bandages are flat and include two adhesive strips separated by a piece of gauze. Other basic bandage configurations include flat pieces of gauze and gauze bandage rolls. Each of these basic bandage types have similar limitations, they have no structure to hold them away from a wound, as such after they are applied they can and will easily touch and potentially damage a wound that they cover. For example a burn on a person's arm when wrapped with a gauze bandage must be adhered to the person's arm using adhesive tape that contacts the person's arm or that contacts the gauze bandage itself. Furthermore, gauze wrapped around an appendage may constrict that appendage and constrict the wound, potentially causing even more damage.

A current issue for burn victims is the lack of oxygenation available to the burn/wound while at the same time covering the wound but not reopening or aggravating the burn wound through removing and replacing the bandage(s). Current bandages hurt the wound by touching the burned area and also disturbs the scabs that are formed. Current band-aids don't stop inadvertent pressure on the wound area, as inadvertent pressure causes the current band-aids to press against the sensitive area of the wound.

Because of these reasons, current bandages often hurt the wound by touching the wound and by disturbing scabs that form on a patient's skin as a burn or wound is healing. Furthermore, current bandages don't stop inadvertent pressure on the wound area. Inadvertent pressure often causes current types of bandages to press against the sensitive area of a wound. When the wound is a burn, the touching of the wound area may damage the patient's skin more than the touching of a scratch or a cut.

Furthermore, a current issue for burn victims is the lack of oxygenation available to the burn/wound while at the same time covering the wound without reopening or aggravating the burn wound when a bandage is worn, removed, and then replaced. This is especially true in the case of second degree burns, which may include blistering that indicates damage has been done to the underlying layers of skin. Disturbance of blisters increases infection and complexity of healing. Undisturbed and oxygenated blisters will rapidly heal.

What are needed are new forms of bandages that minimize how much the bandage touches the wound when covering the wound. This is especially true when the wound being covered is a burn or an injury that spans a large portion of injured skin. These new forms of bandages are defined as sterile wound dressing articles of manufacture herein referred to as Burn Bandage(s) as described to follow.

SUMMARY OF THE PRESENTLY CLAIMED INVENTION

The presently claimed invention relates to a Burn bandage that covers a wound. The Burn Bandage consistent with the presently claimed invention includes a structure that has a shape that circumscribes an area above the skin of a person when it is aligned above a wound such that the structure bridges over the wound after it is aligned above the wound, wherein the structure of the Burn Bandage does not contact the wound. This Burn Bandage also includes a base portion that contacts skin of the person when the structure is aligned above the wound.

This invention is a system, Kit, and article of manufacture for Burn Bandages for burn wounds in which the protective covering does not come into direct contact with the burned area. The covering has holes to allow airflow to the burned area. The apparatus may be secured to the victim using tapes or straps that come into contact with the surrounding non-infected area. The article of manufacture has many forms/factors and can be made adjustable and customized to wounds as needed.

Typically when dressing a burn wound, an ointment is spread over the burned area and gauze is placed over the entirety (wound and ointment). Then a bandage wrap covers up the gauze and fastens it to the burned area. When it is time to replace the bandage and gauze, as well as reapply more ointment, the healing process is disrupted by disturbing newly produced blisters and or scabs and increases the probability of infection, complications and scarring. There is also an increase of infection to the burn area if the gauze or bandage(s) is (are) not sterile or if it/they are not regularly replaced. Also, the standard bandage wrap cannot and does not protect against inadvertent pressure that can both cause pain and disrupt the wound and healing process.

This invention allows a person with a burn wound to apply an ointment to the burned area and determine the size of the Burn Bandage necessary based upon the size of the burned area. This invention creates a covering that may come into direct contact solely with the surrounding area of the burn, i.e. with non-burned tissue. The area of the Burn Bandage that would cover the burned area would be raised. In example, a dome shape or any other raised symmetrical or asymmetrical shape placed above the injured tissue and have holes or airways that would allow oxygen to come in contact with and naturally flow to the burned tissue. The apparatus may be a dome structure manufactured from a clear or transparent plastic like material to allow the patient to physically see the wound through the dome covering. The dome covering may also be constructed from any and all transparent materials that are used for their transparency in optics and in the decorative arts such as but not limited to: borosilicate glass, germanium dioxide, polycarbonate, any form of polyethylene, so-gel and any other appropriate transparent material know in the art. The dome covering may also be manufactured from any material that protects the wound from harmful ultraviolet (UV) rays from the sun that may increase further injury to the wound. Such as, ultraviolet A (UVA) which are long waves that puncture deep into the dermis, or ultraviolet B (UVB) which are short waves that burn the superficial layers of the skin. The dome covering may also be printed with any decorative art, characters, symbols, writings and the like. This apparatus may have a fastener that could wrap around a body part in order to hold it in place or the edges may have a type of adhesive to attach to the surrounding healthy tissue. This would allow a person to safely remove and reapply ointment as needed without disrupting the healing process, increase the speed of the healing process and reduce the possibility of producing a scar.

DETAILED DESCRIPTION

The present disclosure relates to apparatus for covering a burn or other wound in ways that prevent or limit touching the wound. The present disclosure describes Burn Bandages that may include domes or structures that bridge over a wide range of a burn or wound size. The apparatus may be a dome structure manufactured from a clear or transparent plastic like material to allow the patient to physically see the wound through the dome covering. The dome covering may also be constructed from any and all transparent materials that are used for their transparency in optics and in the decorative arts such as but not limited to: borosilicate glass, germanium dioxide, polycarbonate, any form of polyethylene, so-gel and any other appropriate transparent material know in the art. The dome covering may also be manufactured from any material that protects the wound from harmful ultraviolet (UV) rays from the sun that may increase further injury to the wound. Such as, ultraviolet A (UVA) which are long waves that puncture deep into the dermis, or ultraviolet B (UVB) which are short waves that burn the superficial layers of the skin. The dome covering may also be printed with any decorative art, characters, symbols, writings and the like. In certain instances these structures may expand in one or more directions as they are adjusted to fit to a particular burn or wound size. Such bridging structures may include airways, openings, or voids that promote air/oxygen flow to the wound as the Burn Bandage sits upon surfaces or pads that contact healthy surrounding tissue while they cover a wound site. The apparatus may be any shape including, yet not limited to a circle, a rectangle, a square, a hexagon, an octagon, an oval, a cone, a cylinder, have a semi-cylindrical shape, or that have any another geometric shape. Burn Bandages consistent with the present disclosure may come in different sizes in order to cover a wound area. The airways of the apparatus may be placed in any order, pattern, or combination. The airways may be positioned such that they provide oxygenation to a burn or wound area. The apparatus may be secured to the body by methods such as Velcro straps, paper tape, an adhesive, medical tape, elastic bandage, or by any other means.

Figure 1:
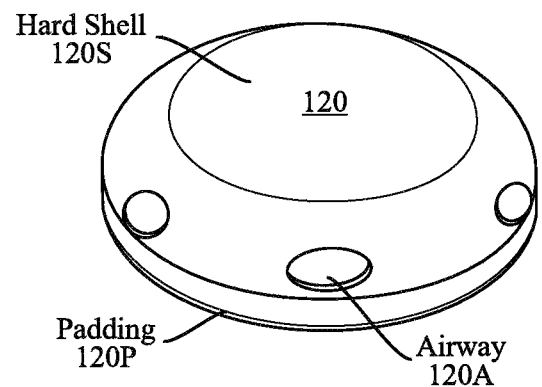
FIG. 1 illustrates several different configurations of Burn Bandages consistent with the present disclosure that minimize or that eliminates the touching of a wound.
Figure 1:
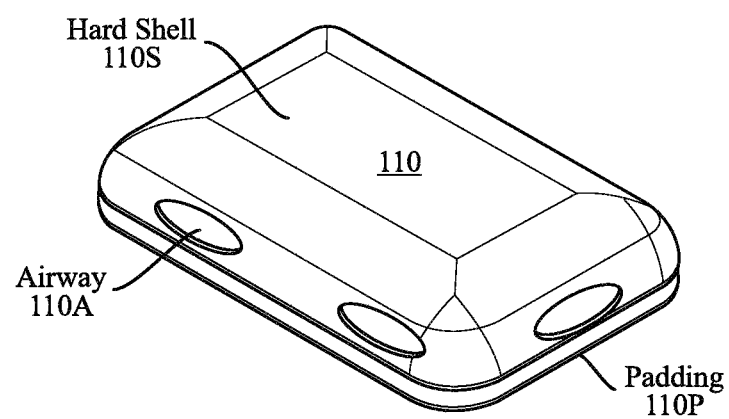
Figure 1:
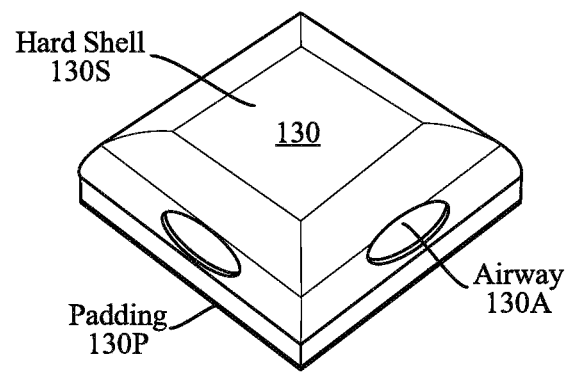

FIG. 1 displays examples of the various shapes that the apparatus could be. These shapes may also be various sizes in order to cover a wide range of burn wounds on the body. The apparatus may be any shape (including but not limited to: circle 120, rectangle 110, square 130, hexagon, octagon, etc.) or size in order to cover the burned area.

FIG. 1 illustrates several different configurations of Burn Bandages consistent with the present disclosure that minimize or that eliminates the touching of a wound. FIG. 1 includes a rectangular shaped Burn Bandage 110, a round Burn Bandage 120, and a square Burn Bandage 130.

Rectangle shape Burn Bandage 110 shows an apparatus that has a hard outer shell that is slightly raised off of the damaged tissue with a hollow center, airways located on all sides in order to allow oxygen to flow into the hollow center and padding around the edges that would come into contact with the healthy tissue. Round Burn Bandage 120 shows an apparatus that is a hard outer shell that is slightly raised off of the damaged tissue with a hollow center, airways located on all sides in order to allow oxygen to flow into the hollow center and padding around the edges that would come into contact with the healthy tissue.

Similarly, Square Burn Bandage 130 figure shows an apparatus that is a hard outer shell that is slightly raised off of the damaged tissue with a hollow center, airways located on all sides in order to allow oxygen to flow into the hollow center and padding around the edges that would come into contact with the healthy tissue.

Note that each respective Burn Bandage 110, 120, and 130 includes a shell (110S, 120S, & 130S) that may be hard (rigid or semi-rigid), a plurality of airways (110A, 120A, & 130A), and a padding area (110P, 120P, & 130P). A person applying a Burn Bandage on a wound could select a Burn Bandage shape and size that best fits a wound when that wound is being bandaged. As such, either the rectangular shape of Burn Bandage 110, the round shape of Burn Bandage 120, or the square shape of Burn Bandage 130 may be selected when a Burn Bandage is applied to protect a wound.

Note that the shells 110S, 120S, and 130S have a structure that includes padded area 110P, 120P, and 130P respectively. Note that these padded areas may contact the skin of a person, circumscribing a perimeter area around a wound. These shell Burn Bandages when applied over a wound may contain an internal area within a perimeter that does not contact the Burn Bandage because of the Burn Bandages structural integrity. Note that the shapes of shells 110S, 120S, and 130S have are uplifted around a perimeter of the Burn Bandage. Such shapes allow the Burn Bandage to be placed above an internal area, protecting a wound contained under those structural shapes.

When shells 110S, 120S, and 130S are touched, force may be transmitted from these shells to pads 110P, 120P, and 130P, such that a force would not be transmitted to the internal area. Because of this, Burn Bandages consistent with the present disclosure protect wounds better than conventional bandages. The padded areas 110P, 120P, and 130P may include an adhesive (not shown) that cause the shell Burn Bandages 110, 120, and 130 to be retained on a person's skin.

Note that Burn Bandages 110, 120, and 130 include airways 110A, 120A, and 130A. Note also that these airways may be open or may be covered with a breathable fabric (such as gauze or filter paper). Airways 110A, 120A, and 130A allow air to flow through Burn Bandages 110, 120, and 130. As such, Burn Bandages 110, 120 and 130 by including airways 110A, 120A, and 130A may increase the ability for a wound to heal by allowing more oxygen to contact the wound. As such, increased oxygen contacting a wound should help limit the growth of bacteria, at least in part because the growth of bacteria may be mitigated by increasing an amount of oxygen that contacts a wound. The shell Burn Bandages 110, 120, and 130 of FIG. 3, thus may both protect the wound from being touched and protect the wound by minimizing bacterial growth.

Figure 2:
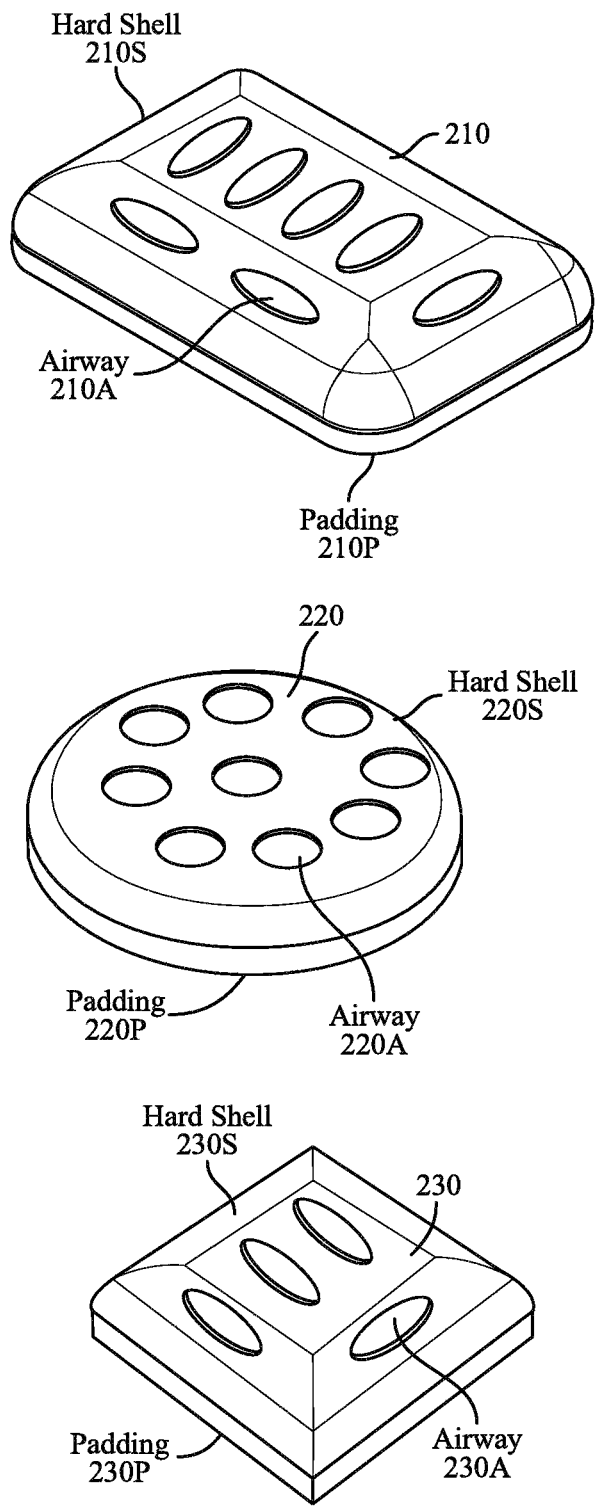
FIG. 2 illustrates several different configurations of Burn Bandages consistent with the present disclosure that minimize or that eliminates the touching of a wound.

FIG. 2 displays examples of the various shapes that the apparatus could be, these shapes may also be various sizes in order to cover a wide range of burn wounds on the body. The apparatus may be any shape (including but not limited to: circle, rectangle, square, hexagon, octagon, etc.) or size in order to cover the burned area. These figures display another example of how the airways may be placed on the apparatus, which may be placed in any order, pattern, or combination to provide oxygenation to the burned area.

Rectangle shape bandage 210 shows an apparatus that has a hard outer shell that is slightly raised off of the damaged tissue with a hollow center, airways located on all sides in order to allow oxygen to flow into the hollow center and padding around the edges that would come into contact with the healthy tissue.

Round Burn Bandage 220 shows an apparatus that is a hard outer shell that is slightly raised off of the damaged tissue with a hollow center, airways located on all sides in order to allow oxygen to flow into the hollow center and padding around the edges that would come into contact with the healthy tissue.

Similarly, Square Burn Bandage 230 figure shows an apparatus that is a hard outer shell that is slightly raised off of the damaged tissue with a hollow center, airways located on all sides in order to allow oxygen to flow into the hollow center and padding around the edges that would come into contact with the healthy tissue.

FIG. 2 illustrates several different configurations of Burn Bandages consistent with the present disclosure that minimize or that eliminates the touching of a wound. The Burn Bandages 210, 220, and 230 of FIG. 2 are similar to the Burn Bandages 110, 120, and 130 of FIG. 1. These Burn Bandages have shells that may be hard, rigid, semi-rigid, or semi-flexible. These Burn Bandages have shells that may be made from UVA or UVB protective materials. Note that rectangular shaped Burn Bandage 210 has shell 210S, note that circular shaped Burn Bandage 220 that has shell 220S, and also note that square shaped Burn Bandage 230 has shell 230S.

Each of the Burn Bandages 210, 220, and 230 of FIG. 2 also include airways 210A, 220A, and 230A. The airways 210A, 220A, and 230A of FIG. 2 are located on upper surfaces of Burn Bandages 210, 220, and 230 where airways 110A, 120A, and 130A are located on a side surface of Burn Bandages 110, 120, and 130 of FIG. 1. As such, airways consistent with the present disclosure may be located on any portion of a Burn Bandage consistent with the present disclosure.

Like the Burn Bandages FIG. 1, the Burn Bandages of FIG. 2 also include pads 210P, 220P, and 230P that provide shelled Burn Bandages 210, 220, and 230 to provide a shielded area because pads 210P, 220P, and 230P allow shells 210S, 220S, and 230S to bridge over a protected internal area. Pads 210P, 220P, and 230P may also include an adhesive that allows them to be set and retained over and around a wound.

Airways may also be provided in Burn Bandages consistent with the present disclosure by including gaps in pads, such as pads 210P, 220P, and 230P allow air flow along a person's skin.

Figure 3:
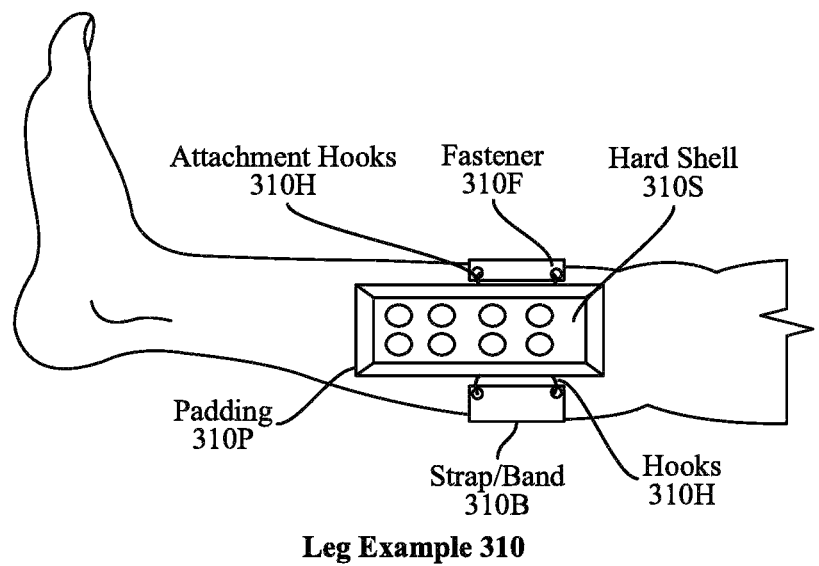
FIG. 3 illustrates two different exemplary Burn Bandages consistent with the present disclosure, one that attaches to a person's leg and another that attaches to a patient's arm.
Figure 3:
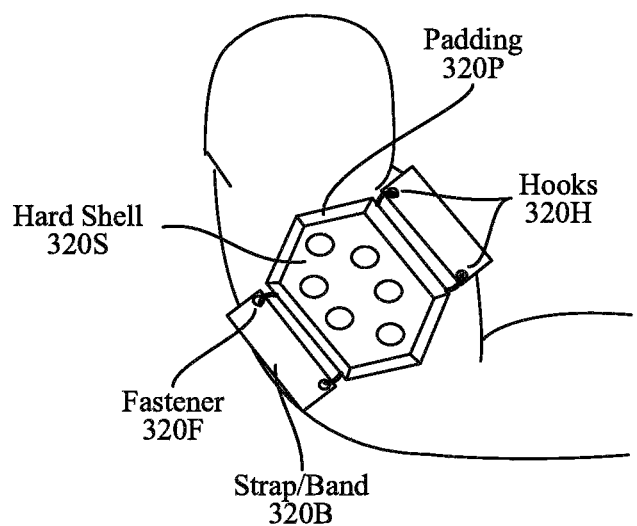

FIG. 3 displays how the apparatus would be fastened to the body (i.e. a leg or an arm). The attachments may be connected to the apparatus through hooks, links, or any other method of securing an attachment for the purpose of fastening the apparatus to the body.

FIG. 3 illustrates two different exemplary Burn Bandages consistent with the present disclosure, one that attaches to a person's leg and another that attaches to a patient's arm. The leg Burn Bandage example 310 includes a hard shell 310S, padding 310P, an attachment fastener portion 310F of an attachment strap/band 310B, and attachment hooks 310H.

Leg Example 310 displays an example of the apparatus fastened to a leg. The apparatus has holes to allow oxygenation. The apparatus contains a hard shell 310S with a hollow interior and padding 310P along the edges that will come into contact with the healthy tissue (the padding 310P may also include an adhesive to attach to the healthy tissue as opposed to using a fastener or strap 310B like the one displayed). The fastener 310F attaches to both sides of the apparatus through hooks 310H attached to the apparatus and connects to the fastener 310F through holes where the hooks 310H can grab a hold of the fastener 310F. The strap or band 310B wraps around the uninjured area of the leg in order to prevent the apparatus from moving or sliding from the desired area.

Arm example 320 displays an example of the apparatus fastened to an arm. The apparatus contains a hard shell 320S with a hollow interior and padding 320P along the edges that will come into contact with the healthy tissue (the padding 320P may also include an adhesive to attach to the healthy tissue as opposed to using a fastener or strap 320B like the one displayed). The fastener 320F attaches to both sides of the apparatus through hooks 320H attached to the apparatus and connects to the strap or band 320B through holes where the hooks 320H can grab a hold of the strap or band 320B. The fastener 320F wraps around the uninjured area of the leg in order to prevent the apparatus from moving or sliding from the desired area.

The arm Burn Bandage example 320 includes similar elements as leg example 310. Arm Burn Bandage 310 includes hard shell 320S, padding 320P, and attachment strap/band 320B that may be used to attach arm Burn Bandage 320 using fastener portion 320F and attachment hooks 310H.

Note that leg Burn Bandage 310 and arm Burn Bandage 320 may be attached using a strap or band where hooks attach a strap to a Burn Bandage via holes. As such, leg Burn Bandage 310 may be attached to a person's leg via fastener portion 310F using hooks 310H and strap/band 310B. Similarly arm Burn Bandage 320 may be attached to a person's arm via fastener portion 320F using hooks 320H and strap/band 320B.

Note that the leg Burn Bandage 310 of FIG. 3 has a rectangular a shape and is positioned to cover an injury on a person's calf. Note that arm Burn Bandage 320 has six sides. Note also that arm Burn Bandage 320 is positioned over the side of a person's bicep. The leg Burn Bandage 310 and the arm Burn Bandage 320 of FIG. 3 illustrate that Burn Bandages of different shapes and sizes may be fit on different body parts based on the location and size of an injury.

While FIG. 3 illustrates hooks (310H & 320H) that attach to a fastening point (310F & 320F) of a strap, other mechanisms useful in connecting a band or a strap to a Burn Bandage may be used: these may include Velcro straps, paper tape, medical tape, an elastic bandage, or other fastening mechanism.

Figure 4:
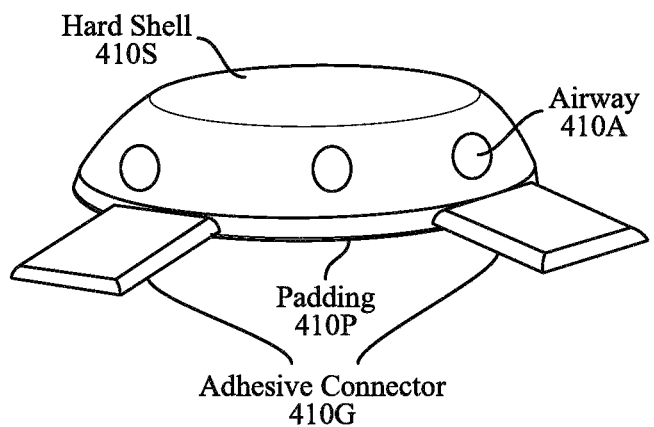
FIG. 4 illustrates a top view and a side view of an exemplary Burn Bandage consistent with the present disclosure.
Figure 4:
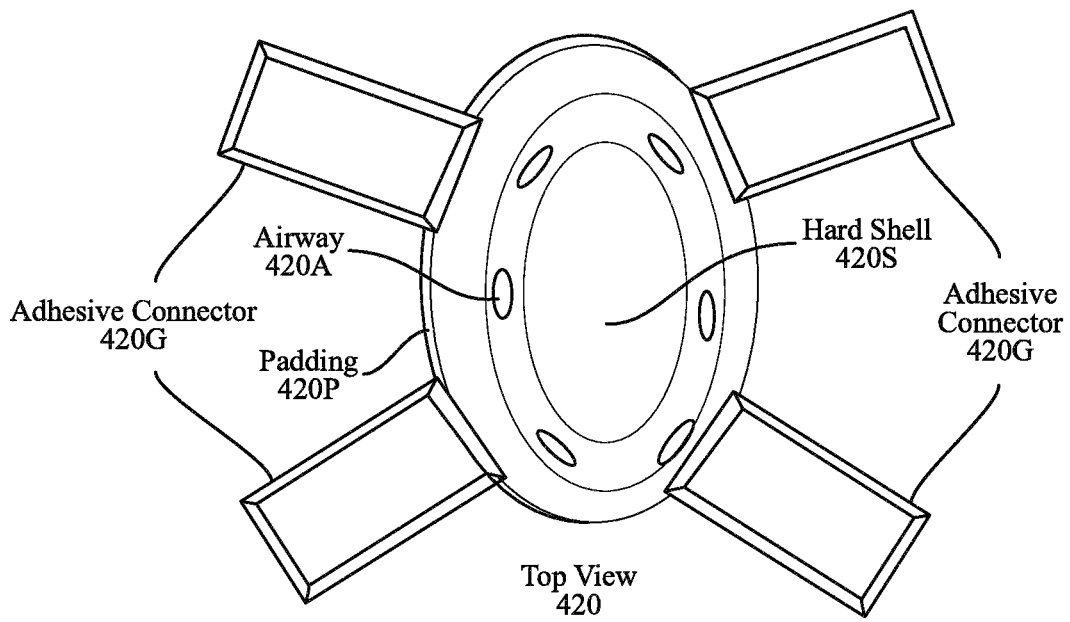

FIG. 4 displays the apparatus with adhesive connectors or fasteners that safely secure the apparatus to the body by connecting to the healthy tissue surrounding the wound. This figure displays one example of how the apparatus may be secured to the body but may also fastened to the body by other methods such as Velcro straps, paper tape, medical tape, elastic bandage, or by any other means.

FIG. 4 illustrates a top view and a side view of an exemplary Burn Bandage consistent with the present disclosure. The Burn Bandage side view 410 has a hard shell 410S, airways 410A, padding 410P, and an adhesive connectors 410G. Adhesive connectors 410G may be used to a Burn Bandage over a burn or other wound. The Burn Bandage top view of FIG. 4 includes hard shell 420S, padding 420P, and adhesive connectors 410G.

Burn Bandage side view 410 shows the side view of the apparatus which has a hard outer shell, which is a sterile plastic, that is slightly raised off of the damaged tissue with a hollow center, airways located on all sides in order to allow oxygen to flow into the hollow center and padding around the edges that would come into contact with the healthy tissue. The apparatus also has adhesive connectors that would safely secure the apparatus in place and would only come into contact with the surrounding healthy tissue. Burn Bandage top view 420 shows the top view of the apparatus with the hard shell, which is hollow and slightly raised, covering up the burned tissue. The padding is on the sides of the apparatus which comes into contact with the healthy tissue. There are airways located on the sides of the apparatus in order to increase oxygen to promote quicker recovery. The apparatus also has adhesive connectors that would safely secure the apparatus in place and would only come into contact with the surrounding healthy tissue.

Here again once a Burn Bandage large enough is identified, it may be placed over a wound, where adhesive connectors may be used to attach that Burn Bandage. When the Burn Bandage is attached it may protect a wound area by circumscribing it in multiple dimensions. Adhesive connectors 410G and 420G may include a layer that covers glue on a lower side of adhesive connectors (410G & 420G) of FIG. 4. Like the paper or plastic strips protecting the glue on a strap of a standard Band-Aid™ bandage, burn/wound Burn Bandages consistent with the present disclosure may include straps that have an adhesive portion covered by a removable cover that can be removed when the Burn Bandage is applied over and around an injury.

Figure 5:
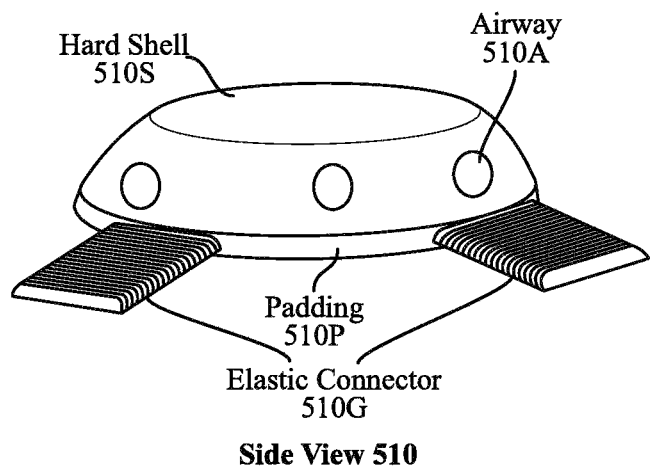
FIG. 5 illustrates a top view and a side view of an exemplary Burn Bandage with adhesive connectors consistent with the present disclosure.
Figure 5:
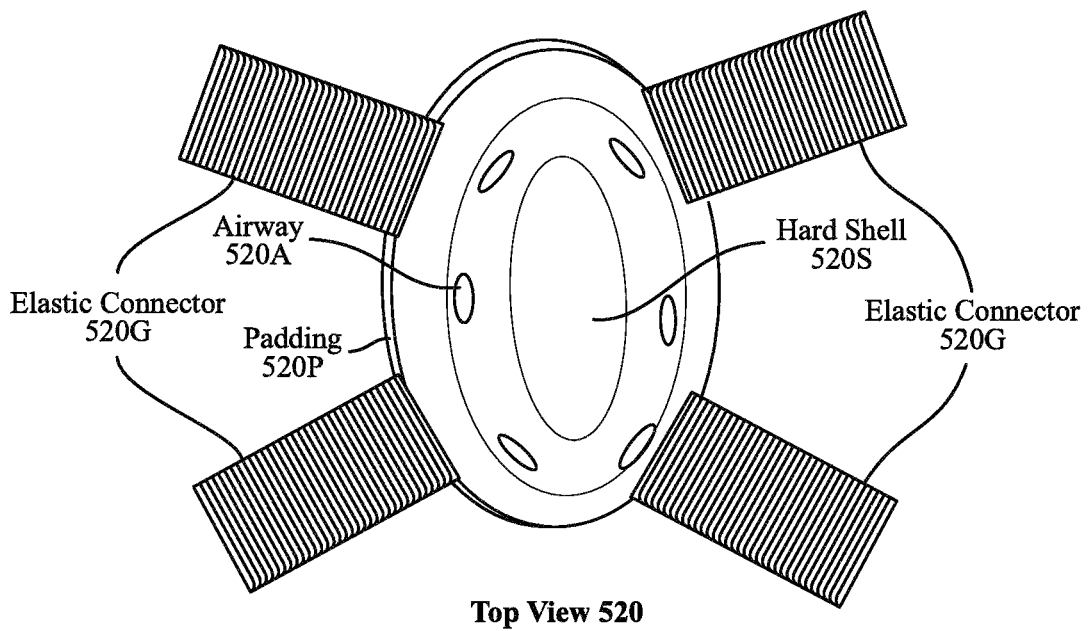

FIG. 5 displays the apparatus with elastic band connectors or fasteners that safely secure the apparatus to the body by connecting to the healthy tissue surrounding the wound. This figure displays one example of how the apparatus may be secured to the body but may also be fastened to the body by other methods such as Velcro straps, paper tape, medical tape, elastic bandage, or by any other means.

FIG. 5 illustrates a top view and a side view of an exemplary Burn Bandage consistent with the present disclosure. The Burn Bandage side view 510 has a hard shell 510S, airways 510A, padding 510P, and an elastic connectors 510G. Elastic connectors 510G may be used to a Burn Bandage over a burn or other wound. The Burn Bandage top view of FIG. 5 includes hard shell 520S, padding 520P, and elastic connectors 510G.

Burn Bandage side view 510 shows the side view of the apparatus which has a hard outer shell, which is a sterile plastic, that is slightly raised off of the damaged tissue with a hollow center, airways located on all sides in order to allow oxygen to flow into the hollow center and padding around the edges that would come into contact with the healthy tissue. The apparatus also has elastic connectors that would safely secure the apparatus in place and would only come into contact with the surrounding healthy tissue. Burn Bandage top view 520 shows the top view of the apparatus with the hard shell, which is hollow and slightly raised, covering up the burned tissue. The padding is on the sides of the apparatus which comes into contact with the healthy tissue. There are airways located on the sides of the apparatus in order to increase oxygen to promote quicker recovery. The apparatus also has elastic connectors that would safely secure the apparatus in place and would only come into contact with the surrounding healthy tissue.

Here again once a Burn Bandage large enough is identified, it may be placed over a wound, where elastic connectors may be used to attach that Burn Bandage. When the Burn Bandage is attached it may protect a wound area by circumscribing it in multiple dimensions. Elastic connectors 510G and 520G may include a layer that covers glue on a lower side of elastic connectors (510G & 520G) of FIG. 5. Like the paper or plastic strips protecting the glue on a strap of a standard Band-Aid™ bandage, burn/wound Burn Bandages consistent with the present disclosure may include straps that have an elastic portion covered by a removable cover that can be removed when the Burn Bandage is applied over and around an injury.

Figure 6:
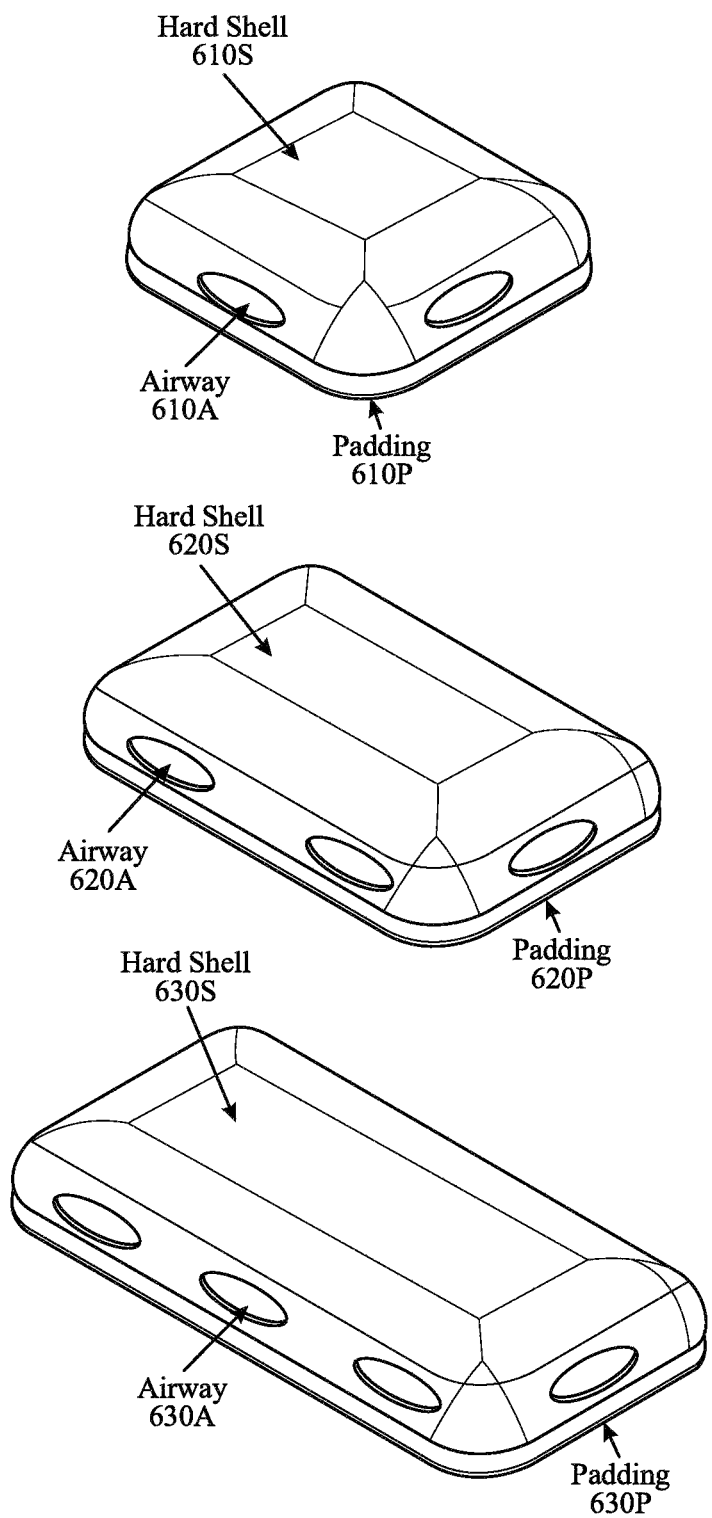
FIG. 6 illustrates several different exemplary sizes that may be used with Burn Bandages with elastic connectors consistent with the present disclosure.

FIG. 6 displays a Kit of various dome sizes that may be used in order to cover a wide range of burn sizes for consumers. The domes range from small to large and may be secured or fastened to the body with either adhesive straps, elastic bands, or an adhesive substance on the surrounding padding. The apparatus may be any shape (including but not limited to: circle, rectangle, square, hexagon, octagon, etc.) or size in order to cover the burned area. The airways of the apparatus may be placed in any order, pattern, or combination to provide oxygenation to the burned area. The apparatus may be secured to the body by methods such as Velcro straps, paper tape, medical tape, elastic bandage, or by any other means.

Figure 7:
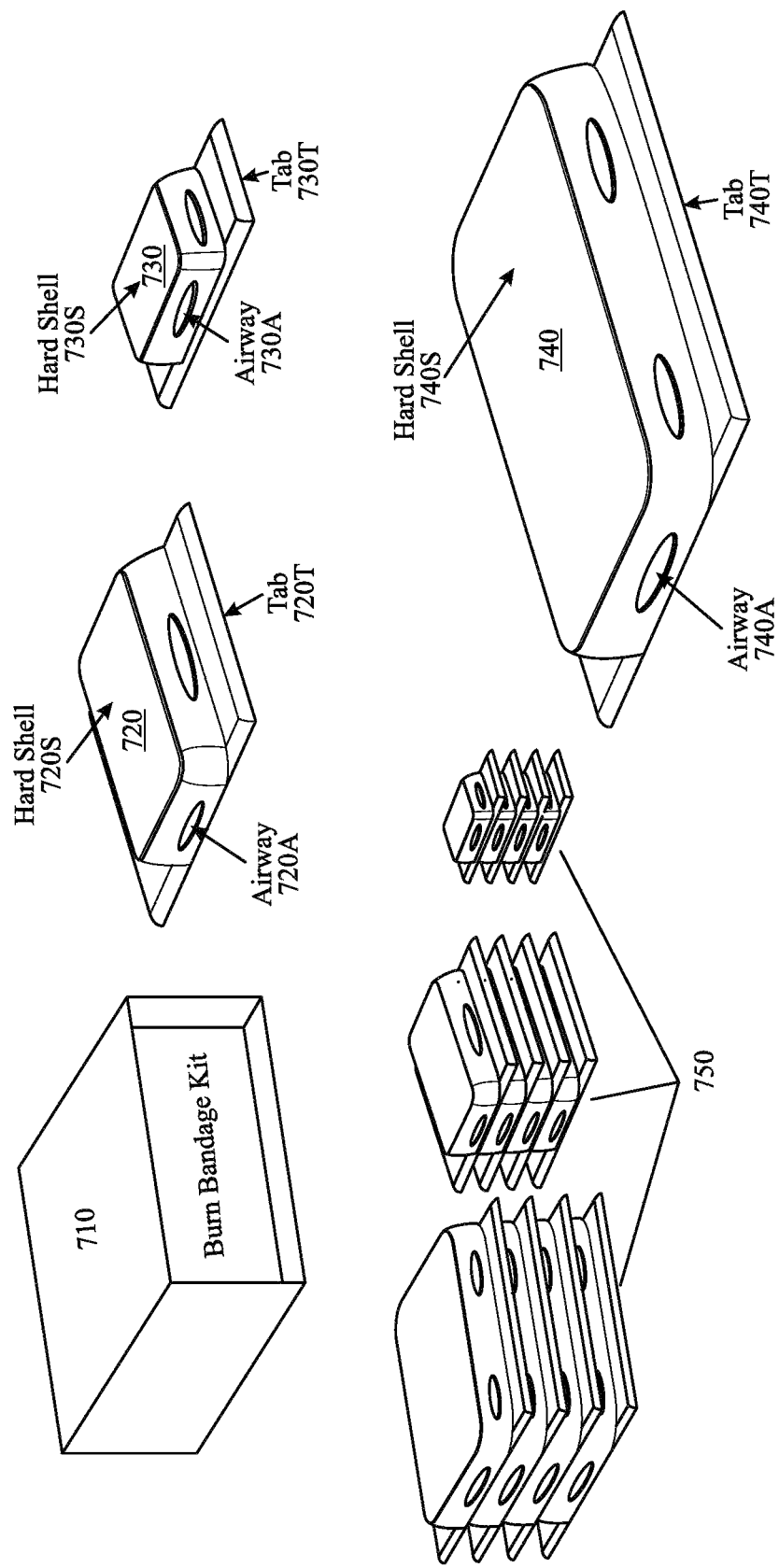
FIG. 7 illustrates an exemplary package that may be used to pack a plurality of Burn Bandages consistent with the present disclosure.

FIG. 7 displays a Kit of Burn Bandages with domes in order to cover a wide range of burn sizes. The apparatus contains a hard outer shell with airways to promote oxygen flow to the wound. The apparatus may be any shape (including but not limited to: circle, rectangle, square, hexagon, octagon, etc.) or size in order to cover the burned area. The airways of the apparatus may be placed in any order, pattern, or combination to provide oxygenation to the burned area. The apparatus may be secured to the body by methods such as Velcro straps, paper tape, medical tape, elastic Burn Bandage, or by any other means.

FIG. 7 illustrates an exemplary package that may be used to pack a plurality of Burn Bandages consistent with the present disclosure. FIG. 7 includes Burn Bandage Kit box 710 that may contain stacks of Burn Bandages 750 of different sizes. Note each of the different Burn Bandage sizes in Burn Bandages stacks 750 all may have similar attributes such as hard shell 720S, 730S, 740S airway 720A, 730A, 740A and tabs 720T, 730T, 740T of Burn Bandage 720, 730, 740 in FIG. 7. The tabs 720T, 730T, 740T of FIG. 7 may itself be a piece that covers an adhesive portion of Burn Bandage 720, 730, 740. In certain instances, when tab 720T, 730T, 740T is removed from Burn Bandage 720, 730, 740 an adhesive portion located around a bottom portion of Burn Bandage 720, 730, 740 may be exposed as a Burn Bandage is placed over a wound. For example, Burn Bandage 720, 730, 740 may include a rectangular padded portion disposed along a rectangular perimeter area that includes an adhesive used to stick Burn Bandage 720, 730, 740 to a person's skin around a wound area.

The stacks of Burn Bandages 750 may be placed in box 710 forming a burn/wound Burn Bandage Kit where tabs 720T, 730T, 740T may help maintain each of a plurality of Burn Bandage stacks in groups of Burn Bandages of different sizes.

Figure 8:
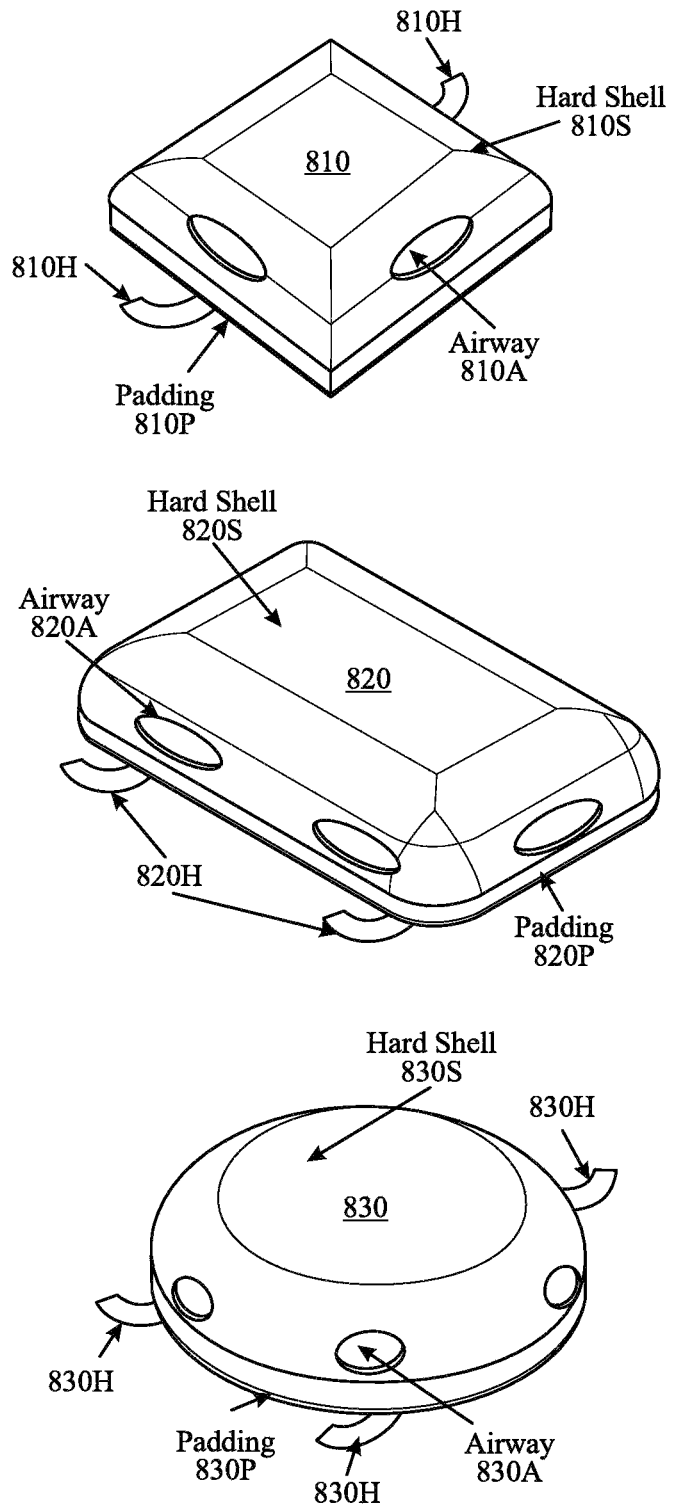
FIG. 8 illustrates several different exemplary Burn Bandages consistent with the present disclosure where hooks may be used to secure the Burn Bandage.

FIG. 8 illustrates a Burn Bandage consistent with the present disclosure where hooks may be used to secure the Burn Bandage. The square Burn Bandage 810 of FIG. 8 includes hard shell 810S, padding 810P, airways 810A, and hooks 810H. Hooks 810H may be permanently attached to Burn Bandage 810 and be positioned so they can be attached to a strap that circumscribes a portion of a person's arm or leg, like the Burn Bandages of FIG. 3, for example. Alternatively such Burn Bandages may be used to cover a wound on a person's torso where hooks attach to straps that wrap around portions of the person's torso.

The rectangle Burn Bandage 820 of FIG. 8 includes hard shell 820S, padding 820P, airways 820A, and hooks 820H. Hooks 820H may be permanently attached to Burn Bandage 820 and be positioned so they can be attached to a strap that circumscribes a portion of a person's arm or leg, like the Burn Bandages of FIG. 3, for example. Alternatively such Burn Bandages may be used to cover a wound on a person's torso where hooks attach to straps that wrap around portions of the person's torso.

The circle Burn Bandage 830 of FIG. 8 includes hard shell 830S, padding 830P, airways 830A, and hooks 830H. Hooks 830H may be permanently attached to Burn Bandage 830 and be positioned so they can be attached to a strap that circumscribes a portion of a person's arm or leg, like the Burn Bandages of FIG. 3, for example. Alternatively, such Burn Bandages may be used to cover a wound on a person's torso where hooks attach to straps that wrap around portions of the person's torso.

FIG. 8 displays a Kit of various dome shapes that may be used in order to cover a wide range of burn shapes for consumers. The domes may include rectangles 820, circles 830, squares 810, or any geometrical shape, etc. and may be secured or fastened to the body with either adhesive straps, elastic bands, or an adhesive substance on the surrounding padding. The apparatus may be any shape (including but not limited to: circle 830, rectangle 820, square 810, hexagon, octagon, etc.) or size in order to cover the burned area. The airways of the apparatus may be placed in any order, pattern, or combination to provide oxygenation to the burned area. The apparatus may be secured to the body by methods such as Velcro straps, paper tape, medical tape, elastic Burn Bandage, or by any other means.

Figure 9:
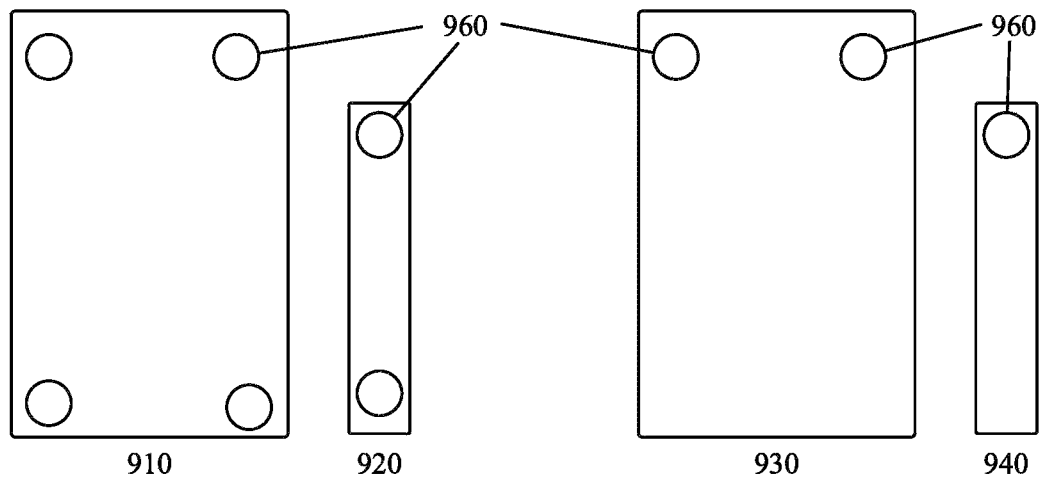
FIG. 9 illustrates several different exemplary straps that may be used with Burn Bandages consistent with the present disclosure.

FIG. 9 displays the various attachments that could be used to secure the apparatus to the body.

FIG. 9 illustrates several different exemplary straps that may be used with Burn Bandages consistent with the present disclosure. FIG. 9 includes straps 910, 920, 930, and 940 where each of these straps includes holes 960 that may be attached to one or more hooks or fasteners. Note that each of these straps may be of different shapes, sizes and lengths.

Strap 910 is an attachment that is a full wrap and connects to both sides of e apparatus and wraps completely around the body part.

Strap 920 is an attachment that is a strap that connects to both sides of the apparatus and stretches across the body part. Strap 930 is an attachment that is a large adhesive wrap that connects to one side of the apparatus and is securely fastened to the body using the adhesive Strap 940 is an attachment that is an adhesive strap that connects to one hook on the apparatus and is securely fastened to the body using the adhesive.

Note that straps 910 and 920 include holes along two different edges, where straps 930 and 940 include holes along a single edge. As such, straps 910 and 920 may wrap around an appendage of a person and be attached to two opposite sides of a burn/wound Burn Bandage of the present disclosure.

Straps 930 and 940 may also include an adhesive portion located on the strap, such that one or more straps could be attached to a Burn Bandage using hooks and holes 960, and be attached to a person's skin via an adhesive portion of straps 930 and 940, for example.

FIG. 9 also includes table 950 that summarizes different features and shapes that different Burn Bandages may include. Note that Burn Bandages consistent with the present disclosure may come in shapes that include, yet are not limited to a rectangular shape, a circular shape, a triangle shape, a square shape, a hexagon shape, and an octagonal shape. Table 950 also illustrates that straps of particular Burn Bandages may be able to full wrap around a body part (a "full wrap" Burn Bandage/strap), may be adhesive straps, and may be an elastic strap.

Table 950 is a table that displays the various attachments that may be used with the various shapes of the apparatus, the shapes are listed vertical and the possible attachments are listed horizontally.

Figure 10:
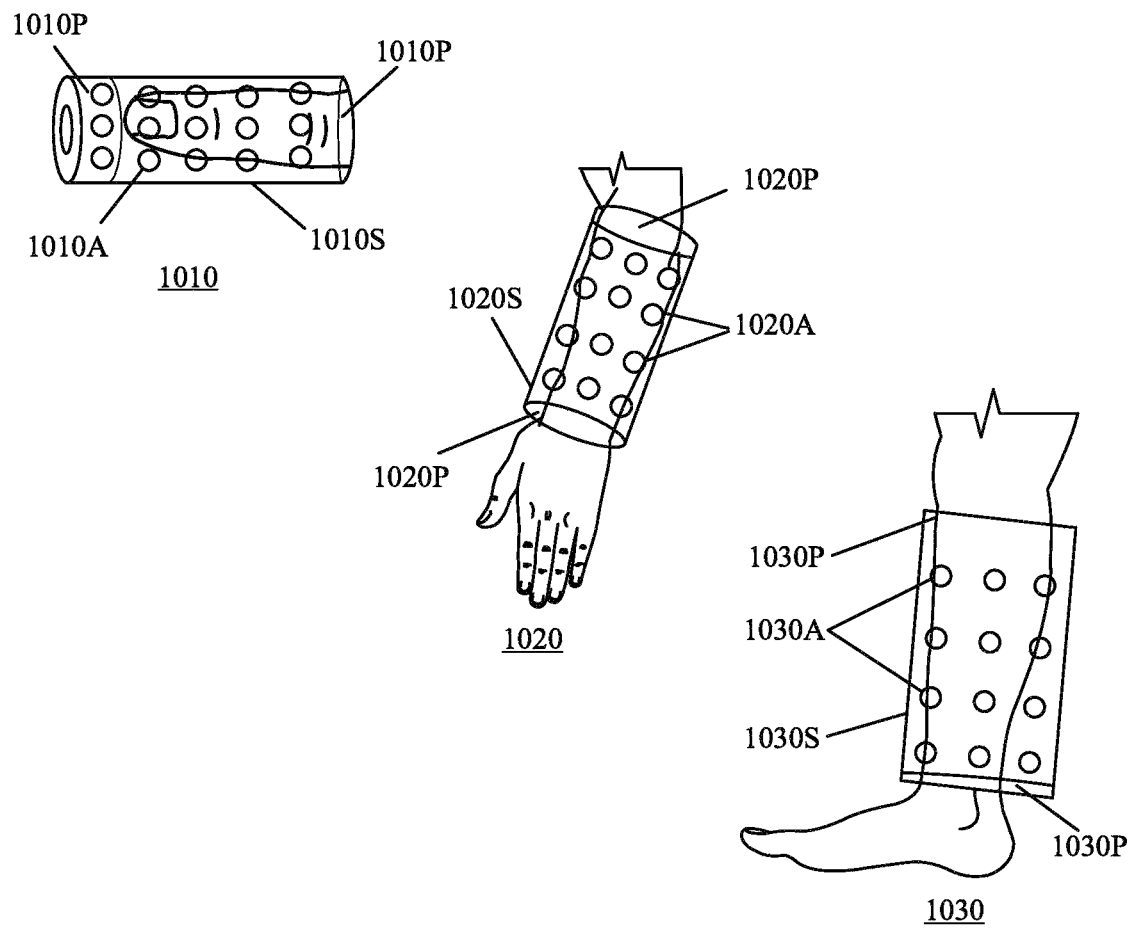
FIG. 10 illustrates different exemplary Burn Bandages that may be in a cylindrical or in a cone shape.

FIG. 10 displays cones, instead of domes, in order to cover a large area of the body that may have a burn wound. The airways of the apparatus may be placed in any order, pattern, or combination to provide oxygenation to the burned area. The apparatus may be secured to the body by methods such as Velcro straps, paper tape, medical tape, elastic Burn Bandage, or by any other means.

Burn Bandage 1010 displays a finger cone in order to protect a burned finger, this may include airways to promote oxygen flow as well as padding surrounding the base of the cone to comfortably secure the cone to the finger. Burn Bandage 1020 displays a forearm cone in order to protect a burned arm, this may include airways to promote oxygen flow as well as padding surrounding the sides of the cone to comfortably secure the cone to the arm.

Burn Bandage 1030 displays a leg cone in order to protect a burned leg, this may include airways to promote oxygen flow as well as padding surrounding the base of the cone to comfortably secure the cone to the leg.

FIG. 10 illustrates different exemplary Burn Bandages that may be in a cylindrical or in a cone shape. The Burn Bandages 1010, 1020, and 1030 of FIG. 10 may predominantly circumscribe an entire appendage of a person. Note that Burn Bandage 1010 covers most of a person's finger, note that Burn Bandage 1020 covers most of a person's forearm, and note that the Burn Bandage 1030 covers most of a person's lower leg. Burn Bandages with a cone shape or a cylindrical shape may include an open side portion that allows the Burn Bandage to be applied from the side of a person's arm or leg without having to be slid over the person's hand or foot.

Burn Bandage 1010 includes airways 1010A, padding portions 1010P, and shell 1010S. Here again shell 1010S may be a hard shell, airways 1010A may allow air to circulate around a burn or wound, and that padding 1010P may flexibly hold Burn Bandage 1010 in a position above the burn or wound area on a person's finger.

Similarly, Burn Bandage 1020 includes airways 1020A, padding portions 1020P, and shell 1020S. Shell 1020S may be a hard or semi-flexible shell, airways 1020A may allow air to circulate around a burn or wound, and padding 1020P may flexibly pad Burn Bandage 1020 in a position above the burn or wound area on a person's forearm.

Note that Burn Bandage 1030 also includes airways 1030A, padding portions 1030P, and shell 1030S. Shell 1030S may be a hard or semi-flexible shell, airways 1030A may allow air to circulate around a burn or wound, and padding 1030P may flexibly pad Burn Bandage 1030 in a position above the burn or wound area on a person's lower leg.

Figure 11:
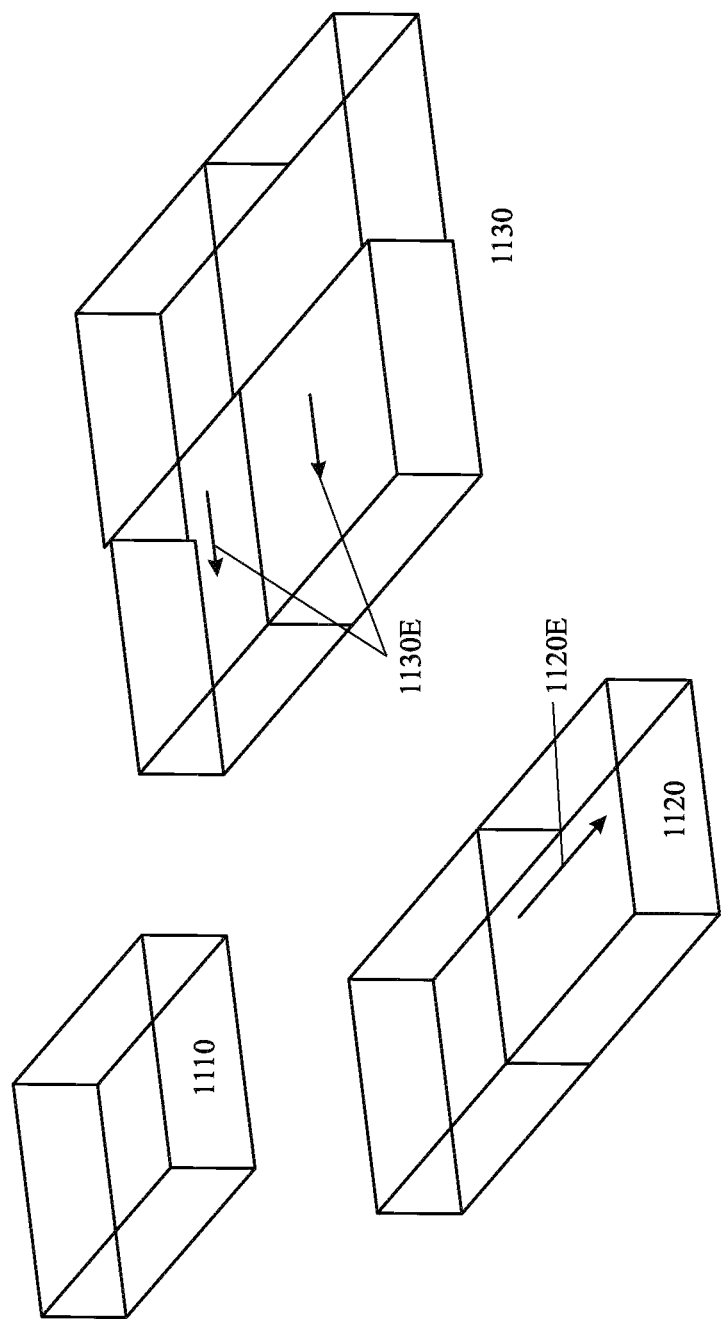
FIG. 11 illustrates exemplary Burn Bandages consistent with the present disclosure that may be used in a standard configuration or may be expanded into other larger configurations.

FIG. 11 displays an expandable apparatus in which the apparatus can slide to create a large or smaller coverage area in order to customize the apparatus depending on the burn size. The expandable apparatus is four separate pieces (i.e. squares) that are connected through tracks on the side of the pieces which lock into place by track guides that are on side of the extendable piece. This allows the apparatus to be expanded and collapsed to the desired size of the user.

Burn Bandage configuration 1110 displays the collapsed apparatus which contains four squares occupying the same area in order to cover a smaller area.

Burn Bandage configuration 1120 displays a slightly expanded apparatus which contains two smaller squares next to each other inside of the rectangle.

Burn Bandage configuration 1130 displays the fully expanded apparatus which has the two hidden squares from configuration 1120 expanded out to form a large square to cover a larger area.

FIG. 11 illustrates exemplary Burn Bandages consistent with the present disclosure that may be used in a standard configuration or may be expanded into other larger configurations. Note that Burn Bandage configuration 1110 is a square Burn Bandage much like Burn Bandage 130 of FIG. 1. When the Burn Bandage of FIG. 11 is used in configuration 1110, it is large enough to cover a wound that spans a first area.

FIG. 11 also illustrates Burn Bandage configuration 1120 where the Burn Bandage of FIG. 11 is expanded, as indicated by arrow 1120E into expanded Burn Bandage configuration 1120. Note that Burn Bandage configuration 1120 is large enough to cover a burn/wound area that is about twice as large as Burn Bandage configuration 1110. As such, the Burn Bandage of FIG. 11 may be expanded like opening a box containing wooden matches, where one piece slide relative to a second piece.

FIG. 11 also illustrates the Burn Bandage of FIG. 11 being expanded in a second direction as illustrated by Burn Bandage configuration 1130. Note that the arrows 1130E identify a direction in which the Burn Bandage of FIG. 11 may be expanded into Burn Bandage configuration 1130. Note that the area covered by Burn Bandage configuration 1130 may cover a wound area that is about four times larger than Burn Bandage configuration 1110.

After the Burn Bandage of FIG. 11 has been adjusted to an appropriate size, it may be placed and secured above a wound in a manner consisted with the present disclosure. Although not illustrated, the Burn Bandage of FIG. 11 may include a shell, airways, and padding similar to other Burn Bandages of the present disclosure.

Figure 12:
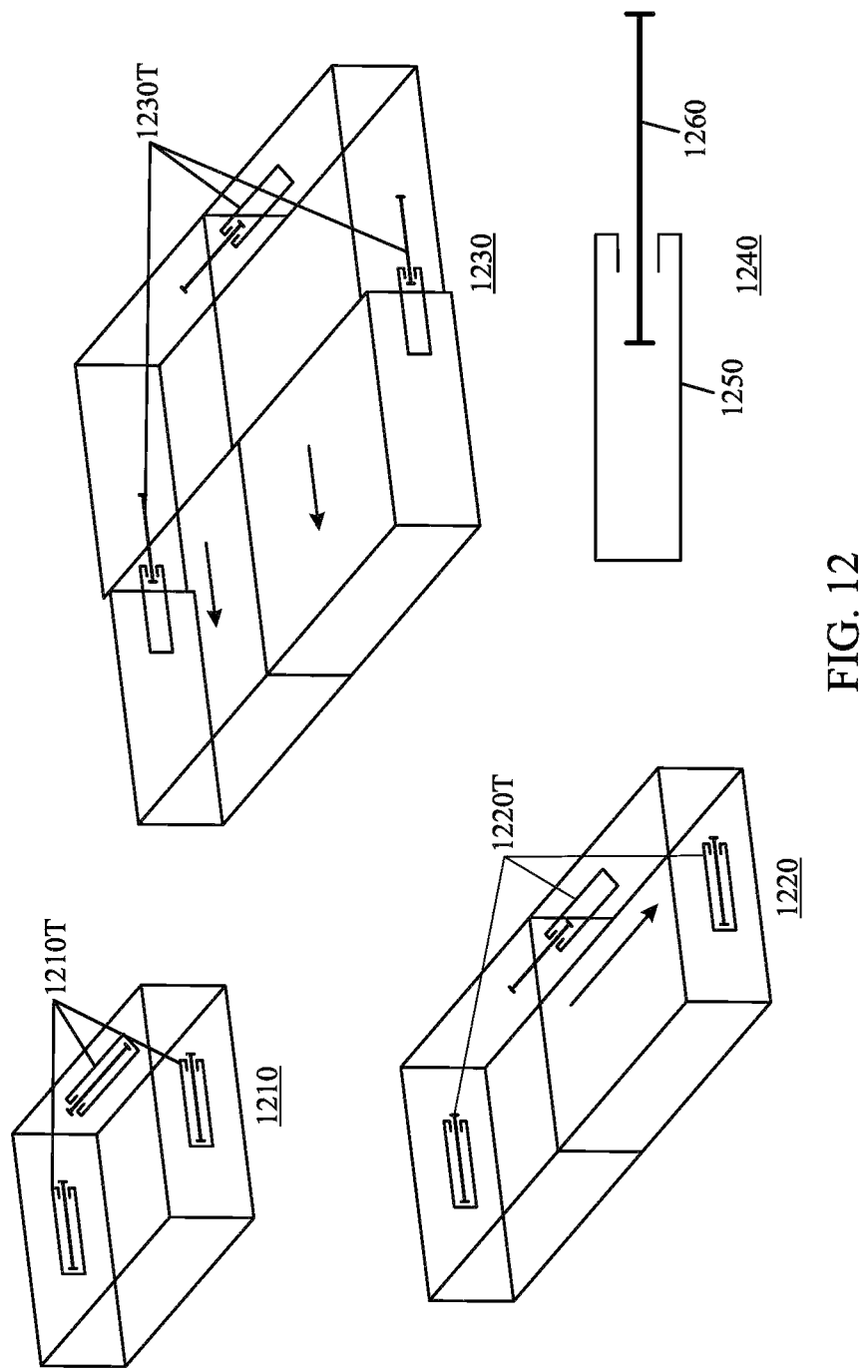
FIG. 12 illustrates exemplary Burn Bandages consistent with the present disclosure that may be used in a standard configuration or may be expanded into other larger configurations using a built in track system.

FIG. 12 illustrates exemplary Burn Bandages consistent with the present disclosure that may be used in a standard configuration or may be expanded into other larger configurations using a built in track system. Note that Burn Bandage configuration 1210 is a square Burn Bandage much like Burn Bandage 130 of FIG. 1. When the Burn Bandage of FIG. 12 is used in configuration 1210, it is large enough to cover a wound that spans a first area. Note that Burn Bandage configuration 1210 also includes a track system in a first configuration 1210T that may be used to expand the Burn Bandage of FIG. 12 from Burn Bandage configuration 1210, to Burn Bandage configuration 1220, and to Burn Bandage configuration 1230.

Please note that Burn Bandage configurations 1210, 1220 and 1230 have airways to promote oxygen flow.

FIG. 12 displays an expandable apparatus in which the apparatus can slide to create a large or smaller coverage area in order to customize the apparatus depending on the burn size. The expandable apparatus is four separate pieces (i.e. squares) that are connected through tracks on the side of the pieces which lock into place by track guides that are on side of the extendable piece. This allows the apparatus to be expanded and collapsed to the desired size of the user.

Burn Bandage configurations 1210 and 1220 displays a slightly expanded apparatus which contains two smaller squares next to each other inside of the rectangle.

Burn Bandage configurations 1230 and 1240 displays the fully expanded apparatus which has the two hidden squares from configuration 1210 expanded out to form a large square to cover a larger area.

FIG. 12 also illustrates Burn Bandage configuration 1220T where the Burn Bandage of FIG. 12 is being expanded, as indicated by arrow in Burn Bandage configuration 1220. The track system of FIG. 12 allows the Burn Bandage of FIG. 12 to be expanded into configuration 1220 by moving the track system of FIG. 12 into configuration 1220T.

Note that Burn Bandage configuration 1220 is large enough to cover a burn/wound area that is about twice as large as Burn Bandage configuration 1210.

FIG. 12 also illustrates the Burn Bandage of FIG. 12 being expanded in a second direction as illustrated by Burn Bandage configuration 1230. Note that the arrows in Burn Bandage configuration 1230 identify a direction in which the Burn Bandage of FIG. 10 may be expanded into Burn Bandage configuration 1230 by moving the track system of FIG. 10 into configuration 1230T. Note that the area covered in Burn Bandage configuration 1230 may cover a wound area that is about four times larger than Burn Bandage configuration 1210.

FIG. 12 also includes an expanded view of a track system 1240 that may be used with a Burn Bandage consistent with the present disclosure. Note that track system 1240 includes slide 1250 and rail 1260 that may be used to expand a Burn Bandage as shown in Burn Bandage configurations 1210, 1220, and 1230. Note that track system 1240 allows rail 1260 to move relative to slide 1250 much like a track system used to open and close a desk drawer.

Please note that Burn Bandage configurations 1210, 1220, 1230 and 1240 have airways to promote oxygen flow.

Figure 13:
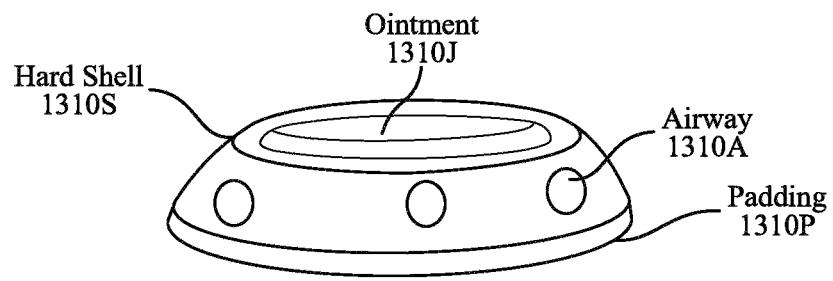
FIG. 13 illustrates an exemplary Burn Bandage consistent with the present disclosure that includes an ointment that may be applied to a burn or wound.
Figure 13:
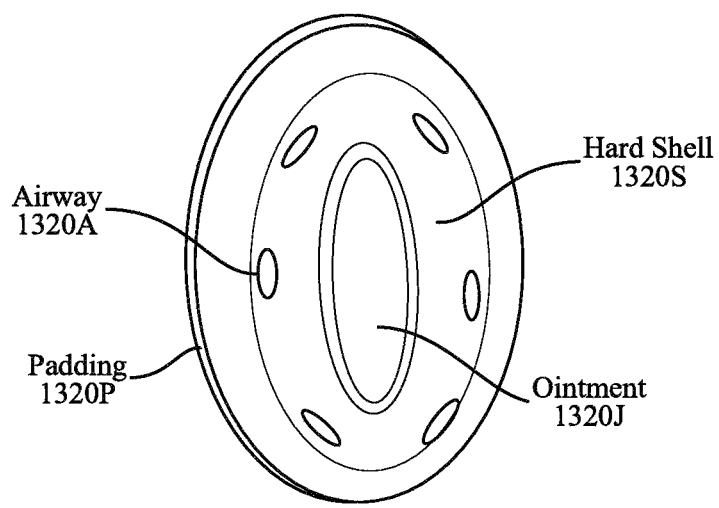

FIG. 13 displays the apparatus in which there is a medical ointment incorporated with the dome that would eventually fall into the wound. The ointment may also be applied to the burned area directly.

Burn Bandage side view 1310 is a side view of the apparatus that has a hard outer shell, which is a sterile plastic, that is slightly raised off of the damaged tissue with a hollow center, airways located on all sides in order to allow oxygen to flow into the hollow center and padding around the edges that would come into contact with the healthy tissue. Also incorporated into the dome is a medical ointment that will eventually fall into the burn wound.

Burn Bandage top view 1320 shows the top view of the apparatus that has a hard shell, which is hollow and slightly raised, covering up the burned tissue. The padding is on the sides of the apparatus which comes into contact with the healthy tissue. There are airways located on the sides of the apparatus in order to increase oxygen to promote quicker recovery. Also incorporated into the dome is a medical ointment that will eventually fall into the burn wound.

FIG. 13 illustrates an exemplary Burn Bandage consistent with the present disclosure that includes an ointment that may be applied to a burn or wound. Note that FIG. 13 includes Burn Bandage side view 1310 and Burn Bandage top view 1320. Burn Bandage side view 1310 includes hard shell 1310S, airways 1310A, padding 1310P, and ointment 1310J. Burn Bandage top view 1320 also includes a hard shell 1320S, airways 1320A, padding 1320P, and ointment 1320J. As such, the Burn Bandage of FIG. 13 may be applied over a wound like other Burn Bandages of the present disclosure.

As the Burn Bandage of FIG. 13 is worn by a person, ointment may flow down with gravity onto a wound. Over time, additional ointment may be added to a space over the wound. In certain instances, the Burn Bandage of FIG. 13 may be gently warmed such that ointment 1310J/1320J liquefies or begins to liquefy, at a specific temperature facilitating an increased flow of ointment onto a wound. In such instances, an ointment may liquefy or begin to liquefy near or above a person's skin. For example, when an ointment begins to liquefy at 90 degrees Fahrenheit (F), the Burn Bandage of FIG. 13 when covering a person's wound may be exposed to air that is warmed to 90 (F) degrees or more before it is blown over a Burn Bandage.

Although, not illustrated in FIG. 13, Burn Bandages consistent with the present disclosure may include a plurality of holes/orifices under ointment 1310J/1320J that allow the ointment to flow onto a wound over time. As such, Burn Bandages consistent with the present disclosure may be used to regulate the amount of ointment that is applied to a wound over time by using different combinations of application temperatures and orifice size.

Figure 14:
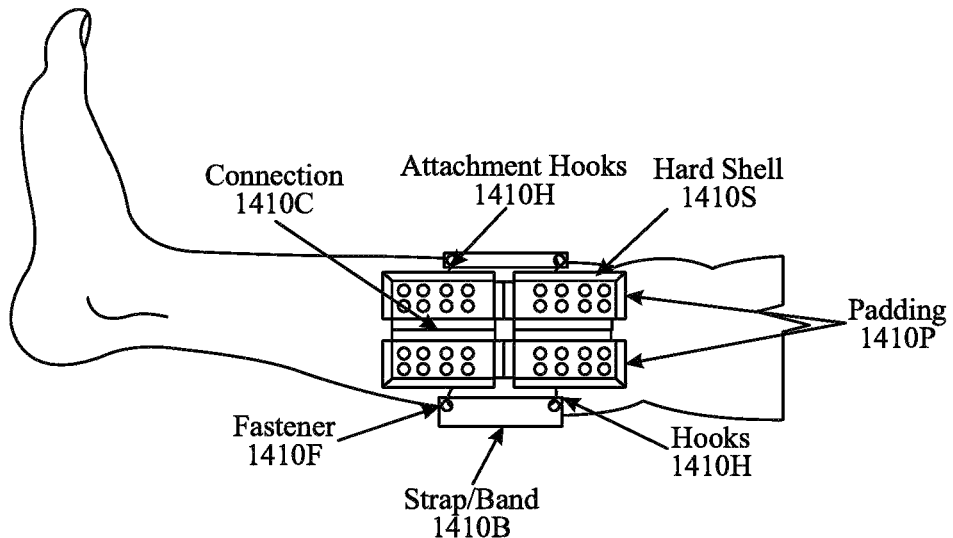
FIG. 14 illustrates exemplary Burn Bandages consistent with the present disclosure that may have various connectable pieces in order to cover wide and unusual wound shapes.
Figure 14:
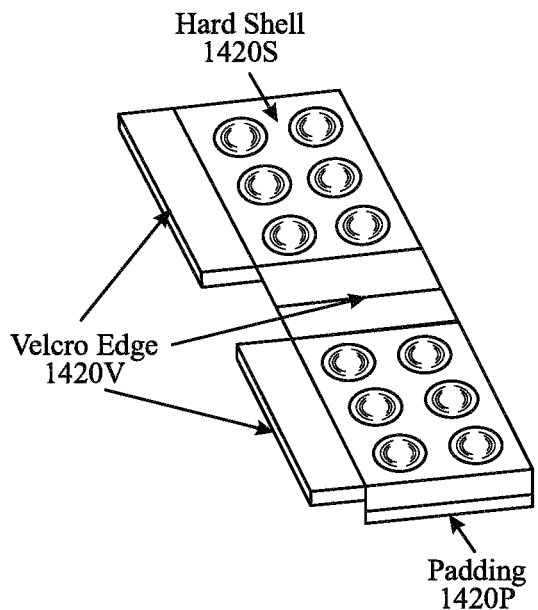

FIG. 14 displays how the apparatus would be fastened to the body (i.e. a leg) using multiple connectable Burn Bandages. The attachments may be connected to the apparatus through hooks, links, or any other method of securing an attachment for the purpose of fastening the apparatus to the body. The various Burn Bandages may be connected to one another using Velcro on the sides of the edges.

FIG. 14 illustrates an exemplary Burn Bandages consistent with the present disclosure, one that attaches to a person's leg. The leg Burn Bandage example 1410 includes a hard shell 1410S, padding 1410P, an attachment fastener portion 1410F of an attachment strap/band 1410B, and attachment hooks 1410H. The leg Burn Bandage also includes a connection 1410C between two (or more) Burn Bandages in order to allow a custom shape of the Burn Bandage.

Leg Example 1410 displays an example of the apparatus fastened to a leg. The apparatus has holes to allow oxygenation. The apparatus contains a hard shell 1410S with a hollow interior and padding 1410P along the edges that will come into contact with the healthy tissue (the padding 1410P may also include an adhesive to attach to the healthy tissue as opposed to using a fastener or strap 1410B like the one displayed). The padding 1410P may be connected to the Burn Bandage through a Velcro connection 1410C. This would allow all of the edges of the Burn Bandage to connect to another Burn Bandage or support the apparatus with the padding 1410P on a healthy portion of skin. The fastener 1410F attaches to both sides of the apparatus through hooks 1410H attached to the apparatus and connects to the fastener 1410F through holes where the hooks 1410H can grab a hold of the fastener 1410F. The strap or band 1410B wraps around the uninjured area of the leg in order to prevent the apparatus from moving or sliding from the desired area.

Note that leg Burn Bandage 1410 may be attached using a strap or band where hooks attach a strap to a Burn Bandage via holes. As such, leg Burn Bandage 1410 may be attached to a person's leg via fastener portion 1410F using hooks 1410H and strap/band 1410B.

Note that the leg Burn Bandage 1410 of FIG. 14 has a rectangular a shape and is positioned to cover an injury on a person's calf. The leg Burn Bandage 1410 of FIG. 14 illustrate that Burn Bandages of different shapes and sizes may be fit on different body parts based on the location and size of an injury.

While FIG. 14 illustrates hooks 1410H that attach to a fastening point 1410F of a strap, other mechanisms useful in connecting a band or a strap to a Burn Bandage may be used: these may include Velcro straps, paper tape, medical tape, an elastic bandage, or other fastening mechanism.

The leg example 1420 displays the connection of two Burn Bandages using a Velcro edge 1420V, which when not being used to connect to another Burn Bandage may flip down to support the apparatus and connect to padding 1420P to improve comfort. The hard shell 1420S has four (which may be more or less depending on the shape of the Burn Bandage) edges that have the ability to rotate to become parallel to the hard shell 1420S to allow the Velcro edge 1420V to connect to another Burn Bandage. The edges may also rotate to be perpendicular to the hard shell 1420S and may have attachable padding 1420P through a Velcro connection to improve comfort of the apparatus.

Figure 15:
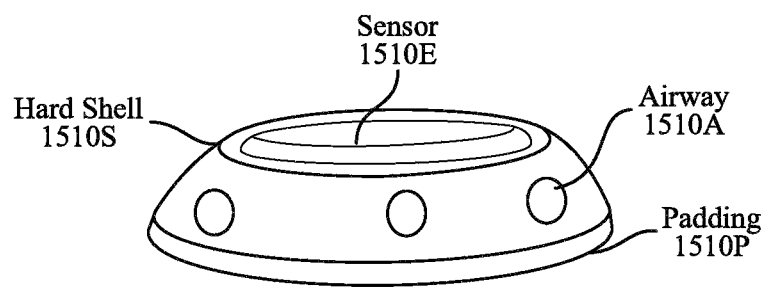
FIG. 15 illustrates exemplary Burn Bandages consistent with the present disclosure that may include sensor(s) embedded in the hard shell.
Figure 15:
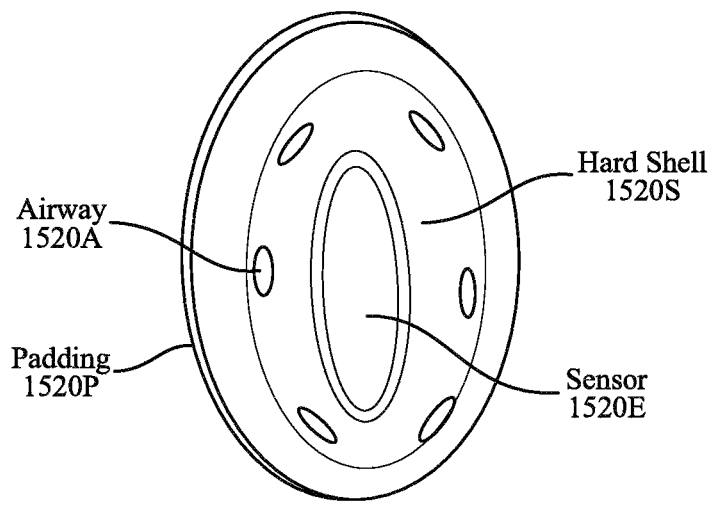

FIG. 15 displays the apparatus in which there is a sensor incorporated with the dome that may monitor the status of the wound. The sensor may also be able to monitor the environment of the wound inside the Burn Bandage.

Burn Bandage side view 1510 is a side view of the apparatus that has a hard outer shell, which is a sterile plastic, that is slightly raised off of the damaged tissue with a hollow center, airways located on all sides in order to allow oxygen to flow into the hollow center and padding around the edges that would come into contact with the healthy tissue. Also incorporated into the dome is a sensor that will track the status of the burn wound and/or the environment inside of the Burn Bandage.

Burn Bandage top view 1520 shows the top view of the apparatus that has a hard shell, which is hollow and slightly raised, covering up the burned tissue. The padding is on the sides of the apparatus which comes into contact with the healthy tissue. There are airways located on the sides of the apparatus in order to increase oxygen to promote quicker recovery. Also incorporated into the dome is a sensor that will track the status of the burn wound and/or the environment inside of the Burn Bandage.

FIG. 15 illustrates an exemplary Burn Bandage consistent with the present disclosure that includes a sensor that may be track the healing status of a burn or wound. Note that FIG. 15 includes Burn Bandage side view 1510 and Burn Bandage top view 1520. Burn Bandage side view 1510 includes hard shell 1510S, airways 1510A, padding 1510P, and sensor 1510E. Burn Bandage top view 1520 also includes a hard shell 1520S, airways 1520A, padding 1520P, and sensor 1520E. As such, the Burn Bandage of FIG. 15 may be applied over a wound like other Burn Bandages of the present disclosure.

As the Burn Bandage of FIG. 15 is worn by a person, the sensor may track the status of the burn or wound or the environment within the Burn Bandage. The sensor 1510E & 1520E may be a moisture sensor to detect if the wound is healing properly or an air quality sensor in order to determine if the air surrounding the wound contains harmful bacteria.

Although, not illustrated in FIG. 15, Burn Bandages consistent with the present disclosure may include a plurality of holes/orifices under sensor 1510E/1520E that allow the sensor to track the air coming into contact with the wound. As such, Burn Bandages consistent with the present disclosure may be used to improve the healing process of the wound by keeping the user/patient more informed of the status of the burn or wound.

Figure 16:
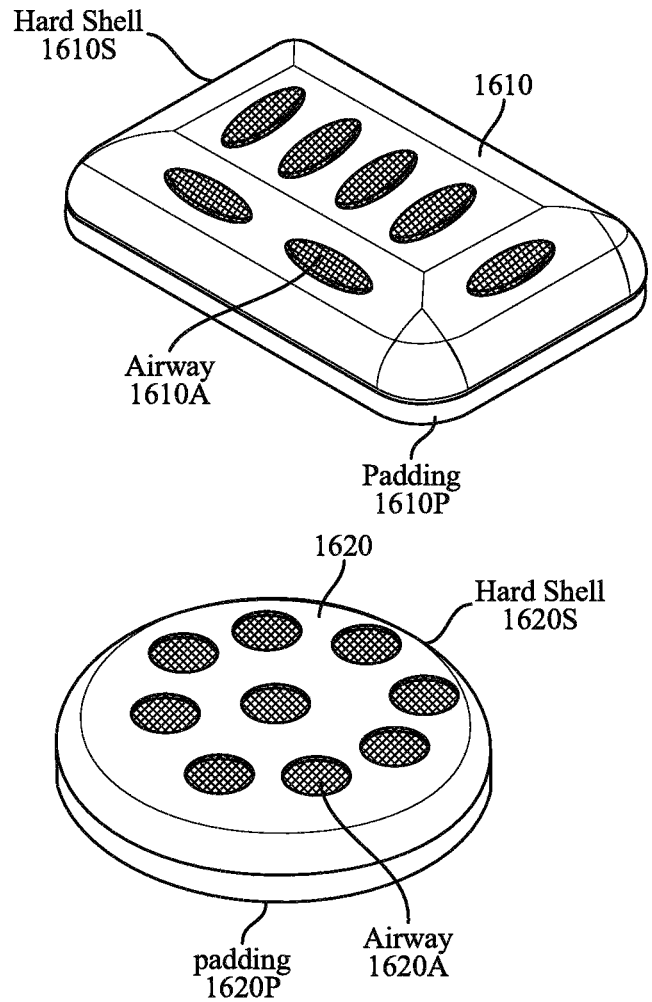
FIG. 16 illustrates exemplary Burn Bandages consistent with the present disclosure that may include coverings over the airways
Figure 16:
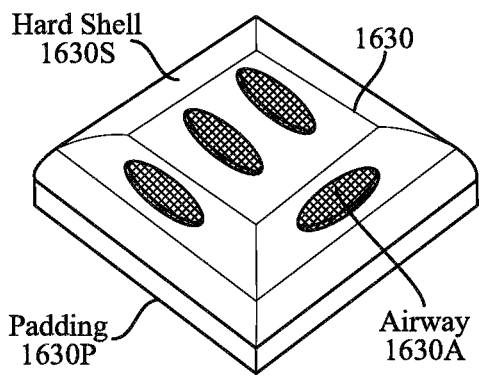

FIG. 16 displays examples of the various shapes that the apparatus could be, these shapes may also be various sizes in order to cover a wide range of burn wounds on the body. The apparatus may be any shape (including but not limited to: circle, rectangle, square, hexagon, octagon, etc.) or size in order to cover the burned area. These figures display another example of how the airways may be placed on the apparatus, which may be placed in any order, pattern, or combination to provide oxygenation to the burned area. These figures display another example of the airways containing a protective film or cloth which provides oxygenation while preventing harmful bacteria from coming into contact with the wound.

Rectangle shape bandage 1610 shows an apparatus that has a hard outer shell that is slightly raised off of the damaged tissue with a hollow center, airways located on all sides in order to allow oxygen to flow into the hollow center and padding around the edges that would come into contact with the healthy tissue. The airways are covered with a protective cloth or film that still provides airflow for oxygenation but prevents bacteria from contacting the wound.

Round Burn Bandage 1620 shows an apparatus that is a hard outer shell that is slightly raised off of the damaged tissue with a hollow center, airways located on all sides in order to allow oxygen to flow into the hollow center and padding around the edges that would come into contact with the healthy tissue. The airways are covered with a protective cloth or film that still provides airflow for oxygenation but prevents bacteria from contacting the wound.

Similarly, Square Burn Bandage 1630 of FIG. 16 shows an apparatus that is a hard outer shell that is slightly raised off of the damaged tissue with a hollow center, airways located on all sides in order to allow oxygen to flow into the hollow center and padding around the edges that would come into contact with the healthy tissue. The airways are covered with a protective cloth or film that still provides airflow for oxygenation but prevents bacteria from contacting the wound.

FIG. 16 illustrates several different configurations of Burn Bandages consistent with the present disclosure that minimize or that eliminates the touching of a wound. The Burn Bandages 1610, 1620, and 1630 of FIG. 16 are similar to the Burn Bandages 210, 220, and 230 of FIG. 2. These Burn Bandages have shells that may be hard, rigid, semi-rigid, or semi-flexible. These Burn Bandages have shells that may be made from UVA or UVB protective materials. Note that rectangular shaped Burn Bandage 1610 has shell 1610S, note that circular shaped Burn Bandage 1620 that has shell 1620S, and also note that square shaped Burn Bandage 1630 has shell 1630S.

Each of the Burn Bandages 1610, 1620, and 1630 of FIG. 16 also include airways 1610A, 1620A, and 1630A. The airways 1610A, 1620A, and 1630A of FIG. 16 contain a protective cloth or film that still provides airflow for oxygenation but prevents bacteria from contacting the wound. As such, airways consistent with the present disclosure may be located on any portion of a Burn Bandage consistent with the present disclosure.

Like the Burn Bandages FIG. 2, the Burn Bandages of FIG. 16 also include pads 1610P, 1620P, and 1630P that provide shelled Burn Bandages 1610, 1620, and 1630 to provide a shielded area because pads 1610P, 1620P, and 1630P allow shells 1610S, 1620S, and 1630S to bridge over a protected internal area. Pads 1610P, 1620P, and 1630P may also include an adhesive that allows them to be set and retained over and around a wound.

Airways may also be provided in Burn Bandages consistent with the present disclosure by including gaps in pads, such as pads 1610P, 1620P, and 1630P containing a protective cloth or film that still provides airflow for oxygenation but prevents bacteria from contacting the wound.

Figure 17:
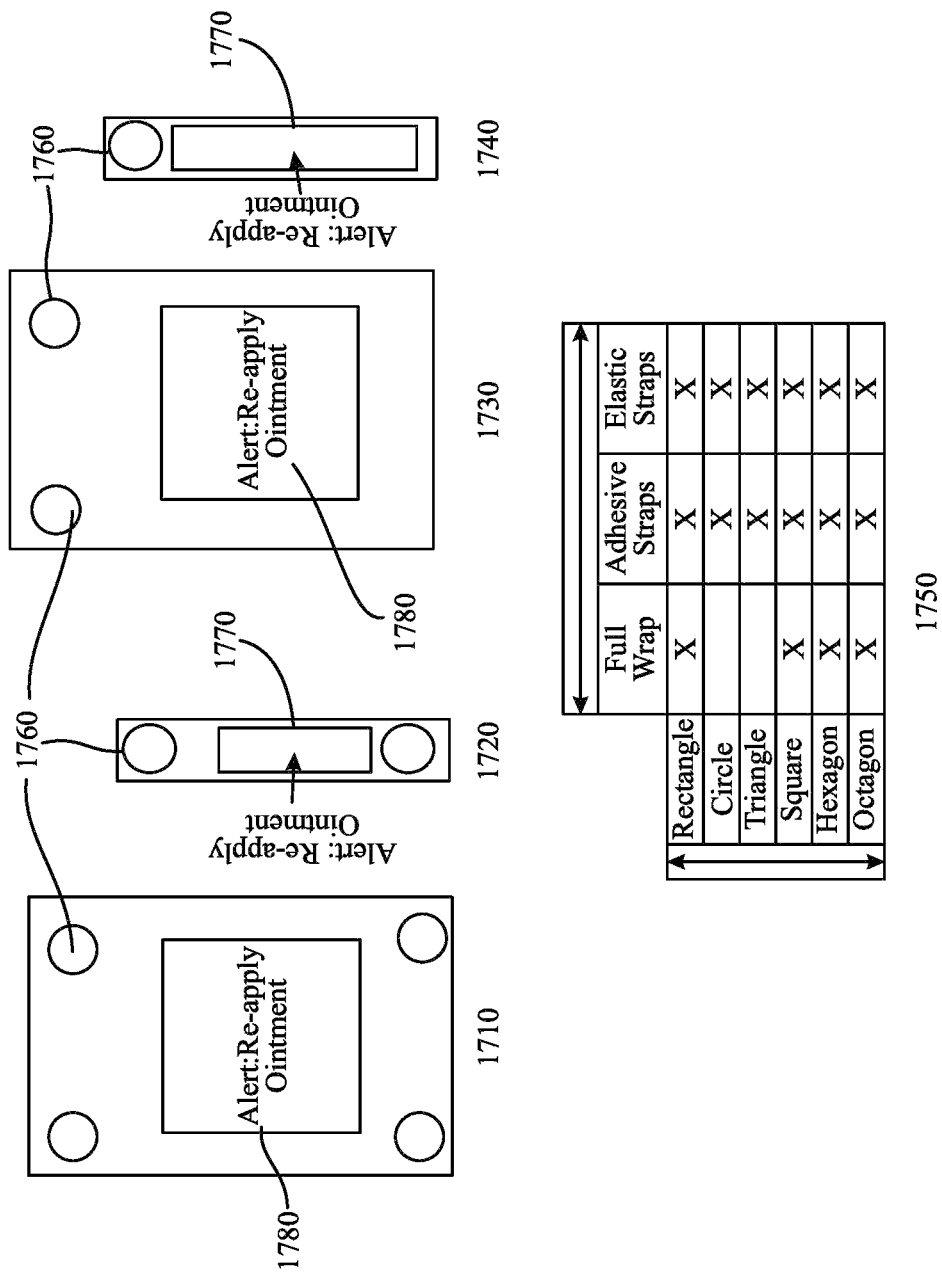
FIG. 17 illustrates exemplary Burn Bandages consistent with the present disclosure that may include sensor(s) embedded in a strap or band

FIG. 17 displays the various smart attachments that could be used to secure the apparatus to the body and inform the user of alerts, notifications, updates, etc. There may be sensors located on the Burn Bandage (i.e. FIG. 15) that may communicate a status, alert, update, or notification to a screen located on a smart band or strap. Also there may be sensors located on the smart band or strap itself and alerts are provided on the screen.

FIG. 17 illustrates several different exemplary smart straps that may be used with Burn Bandages consistent with the present disclosure. FIG. 17 includes straps 1710, 1720, 1730, and 1740 where each of these straps includes holes 1760 that may be attached to one or more hooks or fasteners. Note that each of these straps may be of different shapes, sizes and lengths. Note that each of these straps may use a screen of various sizes in order to inform the user.

Strap 1710 is an attachment that is a full wrap and connects to both sides of the apparatus and wraps completely around the body part. The attachment also includes a screen 1780 that provides notifications, alerts or updates to the user.

Strap 1720 is an attachment that is a strap that connects to both sides of the apparatus and stretches across the body part, which may also include a screen 1770. Strap 1730 is an attachment that is a large adhesive wrap that connects to one side of the apparatus and is securely fastened to the body using the adhesive, and may also include a screen 1780.

Strap 1740 is an attachment that is an adhesive strap that connects to one hook on the apparatus and is securely fastened to the body using the adhesive, and may also include a screen 1770.

Note that straps 1710 and 1720 include holes along two different edges, where straps 1730 and 1740 include holes along a single edge. As such, straps 1710 and 1720 may wrap around an appendage of a person and be attached to two opposite sides of a burn/wound Burn Bandage of the present disclosure.

Straps 1730 and 1740 may also include an adhesive portion located on the strap, such that one or more straps could be attached to a Burn Bandage using hooks and holes 1760, and be attached to a person's skin via an adhesive portion of straps 1730 and 1740, for example.

FIG. 17 also includes table 1750 that summarizes different features and shapes that different Burn Bandages may include. Note that Burn Bandages consistent with the present disclosure may come in shapes that include, yet are not limited to a rectangular shape, a circular shape, a triangle shape, a square shape, a hexagon shape, and an octagonal shape. Table 1750 also illustrates that straps of particular Burn Bandages may be able to full wrap around a body part (a "full wrap" Burn Bandage/strap), may be adhesive straps, and may be an elastic strap.

Table 1750 is a table that displays the various attachments that may be used with the various shapes of the apparatus, the shapes are listed vertical and the possible attachments are listed horizontally.

Figure 18:
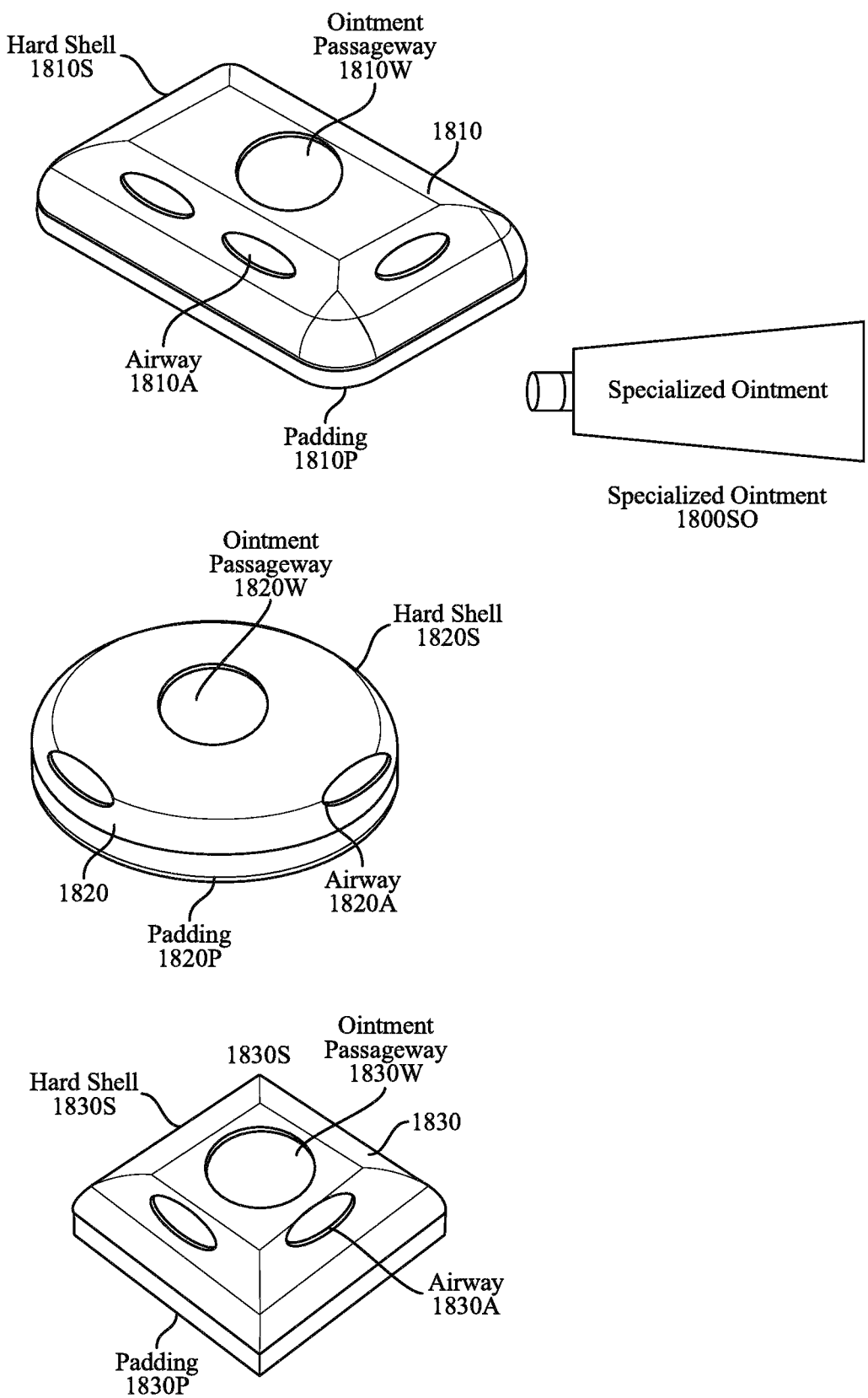
FIG. 18 illustrates exemplary Burn Bandages consistent with the present disclosure that may include a specialized unique ointment passageway through the hard shell for the related unique specialized ointment to be applied to the wound.

FIG. 18 displays examples of the various shapes that the apparatus could be, these shapes may also be various sizes in order to cover a wide range of burn wounds on the body. The apparatus may be any shape (including but not limited to: circle, rectangle, square, hexagon, octagon, etc.) or size in order to cover the burned area. These figures display another example of how the airways may be placed on the apparatus, which may be placed in any order, pattern, or combination to provide oxygenation to the burned area. The apparatus may include a specialized unique ointment passageway to allow the related specialized unique ointment 1800SO to pass through the hard shell covering and be applied to the wound or burn.

Rectangle shape bandage 1810 shows an apparatus that has a hard outer shell that is slightly raised off of the damaged tissue with a hollow center, airways located on all sides in order to allow oxygen to flow into the hollow center and padding around the edges that would come into contact with the healthy tissue. Also, the apparatus may include a specialized unique ointment passageway 1810W to allow the related specialized unique ointment 1800SO to pass through the hard shell covering and be applied to the wound or burn.

Round Burn Bandage 1820 shows an apparatus that is a hard outer shell that is slightly raised off of the damaged tissue with a hollow center, airways located on all sides in order to allow oxygen to flow into the hollow center and padding around the edges that would come into contact with the healthy tissue. Also, the apparatus may include a specialized unique ointment passageway 1820W to allow the related specialized unique ointment 1800SO to pass through the hard shell covering and be applied to the wound or burn.

Similarly, Square Burn Bandage 1830 figure shows an apparatus that is a hard outer shell that is slightly raised off of the damaged tissue with a hollow center, airways located on all sides in order to allow oxygen to flow into the hollow center and padding around the edges that would come into contact with the healthy tissue. Also, the apparatus may include a specialized unique ointment passageway 1830W to allow the related specialized unique ointment 1800SO to pass through the hard shell covering and be applied to the wound or burn.

FIG. 18 illustrates several different configurations of Burn Bandages consistent with the present disclosure that minimize or that eliminates the touching of a wound. The Burn Bandages 1810, 1820, and 1830 of FIG. 18 are similar to the Burn Bandages 110, 120, and 130 of FIG. 1. These Burn Bandages have shells that may be hard, rigid, semi-rigid, or semi-flexible. These Burn Bandages have shells that may be made from UVA or UVB protective materials. Note that rectangular shaped Burn Bandage 1810 has shell 1810S, note that circular shaped Burn Bandage 1820 that has shell 1820S, and also note that square shaped Burn Bandage 1830 has shell 1830S.

Each of the Burn Bandages 1810, 1820, and 1830 of FIG. 18 also include airways 1810A, 1820A, and 1830A. The airways 1810A, 1820A, and 1830A of FIG. 18 are located on lower surfaces of Burn Bandages 1810, 1820, and 1830 where airways 110A, 120A, and 130A are located on a side surface of Burn Bandages 110, 120, and 130 of FIG. 1. Also, the apparatus may include a specialized unique ointment passageways 1810W, 1820W, 1830W to allow the related specialized unique ointment 1800SO to pass through the hard shell covering and be applied to the wound or burn. As such, airways consistent with the present disclosure may be located on any portion of a Burn Bandage consistent with the present disclosure.

Like the Burn Bandages FIG. 1, the Burn Bandages of FIG. 18 also include pads 1810P, 1820P, and 1830P that provide shelled Burn Bandages 1810, 1820, and 1830 to provide a shielded area because pads 1810P, 1820P, and 1830P allow shells 1810S, 1820S, and 1830S to bridge over a protected internal area. Pads 1810P, 1820P, and 1830P may also include an adhesive that allows them to be set and retained over and around a wound.

Airways may also be provided in Burn Bandages consistent with the present disclosure by including gaps in pads, such as pads 1810P, 1820P, and 1830P allow air flow along a person's skin.

Figure 19:
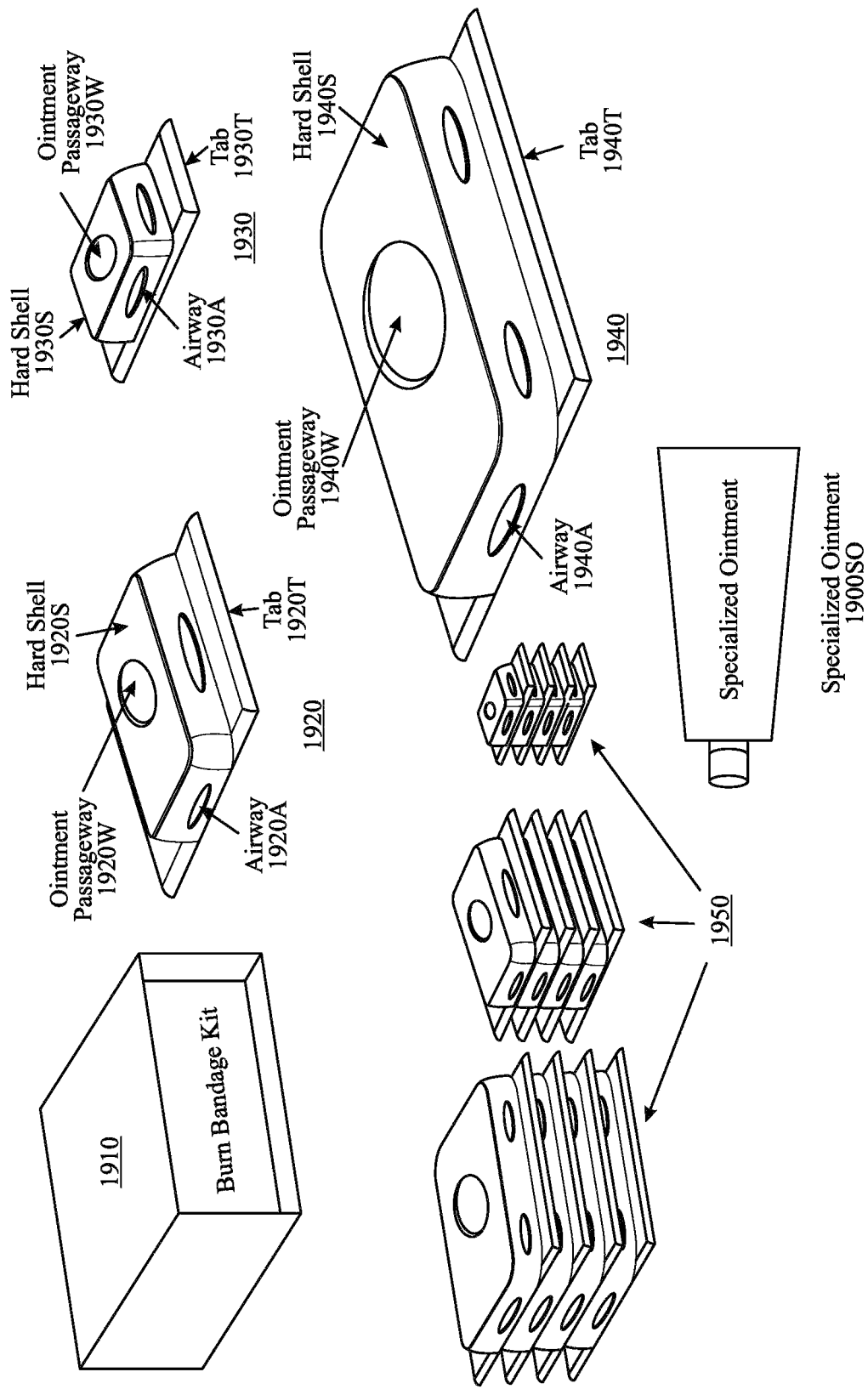
FIG. 19 illustrates an exemplary package that may be used to pack a plurality of Burn Bandages along with the related unique specialized ointment to be applied through the specialized unique ointment passageway consistent with the present disclosure.

FIG. 19 displays a Kit of Burn Bandages with domes in order to cover a wide range of burn sizes. The apparatus contains a hard outer shell with airways to promote oxygen flow to the wound. The apparatus may be any shape (including but not limited to: circle, rectangle, square, hexagon, octagon, etc.) or size in order to cover the burned area. The airways of the apparatus may be placed in any order, pattern, or combination to provide oxygenation to the burned area. The apparatus may be secured to the body by methods such as Velcro straps, paper tape, medical tape, elastic Burn Bandage, or by any other means. The apparatus may include a specialized unique ointment passageway to allow the application of a related specialized unique ointment to the damaged skin without the removal of the apparatus.

FIG. 19 illustrates an exemplary package that may be used to pack a plurality of Burn Bandages consistent with the present disclosure. FIG. 19 includes Burn Bandage Kit box 1910 that may contain stacks of Burn Bandages 1950 of different sizes. Note each of the different Burn Bandage sizes in Burn Bandages stacks 1950 all may have similar attributes such as hard shell 1920S, 1930S, 1940S airway 1920A, 1930A, 1940A, tabs 1920T, 1930T, 1940T and specialized unique ointment passageways 1920W, 1930W, 1940W of Burn Bandage 1920, 1930, 1940 in FIG. 19. The tabs 1920T, 1930T, 1940T of FIG. 19 may itself be a piece that covers an adhesive portion of Burn Bandage 1920, 1930, 1940. In certain instances, when tab 1920T, 1930T, 1940T is removed from Burn Bandage 1920, 1930, 1940 an adhesive portion located around a bottom portion of Burn Bandage 1920, 1930, 1940 may be exposed as a Burn Bandage is placed over a wound. For example, Burn Bandage 1920, 1930, 1940 may include a rectangular padded portion disposed along a rectangular perimeter area that includes an adhesive used to apply the Burn Bandage 1920, 1930, 1940. The Burn Bandage 1920, 1930, 1940, may include specialized unique ointment passageways 1920W, 1930W, 1940W in which the related specialized unique ointment 1900SO can be passed through the Burn Bandage 1920, 1930, 1940 and applied to the burned or damaged skin that is being covered.

The stacks of Burn Bandages 1950 may be placed in box 1910 forming a burn/wound Burn Bandage Kit where tabs 1920T, 1930T, 1940T may help maintain each of a plurality of Burn Bandage stacks in groups of Burn Bandages of different sizes.

Please note that the related specialized unique ointment 1800SO, 1900SO may be included and packaged in Burn Bandage Kit 1910 and/or packaged and sold separately.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claims appended hereto.

What is claimed is:

1. An apparatus that promotes healing of a wound, the apparatus comprising:
    a shell structure including an ointment passageway configured to receive an ointment and to convey flow of the ointment toward the wound;
    a track system configured to slide a first portion of the shell structure relative to a second portion of the shell structure to adjust a size of the shell structure based on a size of the wound; and
    an attachment mechanism configured to maintain an alignment of the shell structure relative to the wound to prevent the shell structure from touching the wound as the ointment flows toward the wound.

2. An apparatus that promotes healing of a wound, the apparatus comprising:
    a structure configured to circumscribe at least a portion of a body part of a person and to cover at least a portion of the wound, the structure including an ointment passageway configured to receive an ointment and to convey flow of the ointment toward the wound;
    a track system configured to slide a first portion of the structure relative to a second portion of the structure to adjust a size of the structure based on a size of the wound; and
    an attachment mechanism configured to maintain an alignment of the structure relative to a location of the wound to prevent the structure from touching the wound as the ointment flows toward the wound.

3. The apparatus of claim 2, the apparatus further comprising one or more tabs extending horizontally from a base of the structure, wherein the one or more tabs are configured to align a stacking arrangement.

4. The apparatus of claim 2, wherein the structure includes a transparent material.

5. The apparatus of claim 2, wherein the structure includes a hard material.

6. The apparatus of claim 2, further comprising padding that is located on a base of the structure and that is configured to contact skin of a person.

7. The apparatus of claim 2, wherein the structure is configured to bridge over the wound to avoid contact with the wound.

8. The apparatus of claim 2, further comprising a sensor that senses a condition associated with the wound.

9. The apparatus of claim 8, further comprising a circuitry coupled to the sensor, the circuitry configured to generate an alert to be communicated.

10. The apparatus of claim 9, wherein the alert requests re-application of the ointment.

11. The apparatus of claim 9, further comprising a screen, wherein the alert is configured to be communicated using the screen.

12. The apparatus of claim 8, wherein the sensor is configured to sense air located in a vicinity of the wound.

13. The apparatus of claim 8, wherein the sensor is configured to sense bacteria.

14. The apparatus of claim 8, wherein the sensor is configured to sense moisture content.

15. The apparatus of claim 2, further comprising one or more airways in the structure, the one or more airways configured to convey air through the structure toward the wound.

16. The apparatus of claim 15, wherein at least a first airway of the one or more airways includes a filter configured to filter the air that is conveyed through at least the first airway.

17. The apparatus of claim 16, wherein the filter reduces passage of at least one of pathogens or particles from the air that is conveyed through at least the first airway toward the wound.

18. The apparatus of claim 2, further comprising a sensor that is configured to assist in identifying whether the wound is healing properly.

19. The apparatus of claim 2, wherein the track system is configured to slide the first portion of the structure relative to the second portion of the structure to expand the size of the structure.

20. The apparatus of claim 2, wherein the track system is configured to slide the first portion of the structure relative to the second portion of the structure to contract the size of the structure.

21. The apparatus of claim 2, wherein the attachment mechanism includes an adhesive.

22. The apparatus of claim 2, wherein the attachment mechanism includes a band configured to wrap around the body part of a person.

23. The apparatus of claim 2, wherein the structure includes a material configured to protect the wound from ultraviolet rays.

24. The apparatus of claim 2, wherein a shape of the structure includes at least one of a rectangular shape, geometrical shape, a curved shape, a circular shape, a triangle shape, a square shape, a hexagon shape, an octagonal shape, a conical shape, or a cylindrical shape.

25. The apparatus of claim 2, wherein the structure includes at least one of a rigid material, a flexible material, a semi-flexible material, or a semi-rigid material.

26. The apparatus of claim 2, wherein the structure includes a container that contains a portion of the ointment.

27. The apparatus of claim 2, wherein an outside surface of the structure is printed with at least one of decorative art, a character, a symbol, or writing.

\* \* \* \* \*